(12) United States Patent
Gimble et al.

(10) Patent No.: US 8,313,743 B2
(45) Date of Patent: Nov. 20, 2012

(54) USE OF ADIPOSE TISSUE-DERIVED STROMAL CELLS IN SPINAL FUSION

(75) Inventors: Jeffrey M. Gimble, Baton Rouge, LA (US); Mandi Lopez, Saint Gabriel, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 42 days.

(21) Appl. No.: 12/791,537

(22) Filed: Jun. 1, 2010

(65) Prior Publication Data

US 2011/0076330 A1 Mar. 31, 2011

Related U.S. Application Data

(63) Continuation of application No. 11/194,270, filed on Aug. 1, 2005, now abandoned.

(51) Int. Cl.
*A61K 35/12* (2006.01)

(52) U.S. Cl. .................. 424/93.7; 424/574; 623/17.11; 623/23.58

(58) Field of Classification Search ............... 424/93.7, 424/574; 623/17.11, 23.58
See application file for complete search history.

(56) References Cited

U.S. PATENT DOCUMENTS

| | | | |
|---|---|---|---|
| 6,100,047 A | 8/2000 | Wilkison et al. | |
| 6,153,432 A | 11/2000 | Halvorsen et al. | |
| 6,242,200 B1 | 6/2001 | Wilkison et al. | |
| 6,391,297 B1 | 5/2002 | Halvorsen | |
| 6,429,013 B1 | 8/2002 | Halvorsen et al. | |
| 6,492,130 B1 | 12/2002 | Wilkison et al. | |
| 6,555,374 B1 | 4/2003 | Gimble et al. | |
| 6,569,633 B1 | 5/2003 | Wilkison et al. | |
| 6,777,231 B1 * | 8/2004 | Katz et al. | 435/325 |
| 6,841,150 B2 | 1/2005 | Halvorsen et al. | |
| 7,595,043 B2 * | 9/2009 | Hedrick et al. | 424/93.7 |
| 2005/0058632 A1 | 3/2005 | Hedrick et al. | |
| 2005/0136042 A1 | 6/2005 | Betz et al. | |
| 2006/0045872 A1 | 3/2006 | Miguel et al. | |

FOREIGN PATENT DOCUMENTS

| | | |
|---|---|---|
| WO | WO 2006/009452 A2 | 1/2006 |
| WO | WO 2006/014159 A2 | 2/2006 |

OTHER PUBLICATIONS

Aust et al., "Yield of human adipose-derived adult stem cells from liposuction aspirates", *Cytotherapy*, 6:1-8 (2004).
Cowan et al., "Adipose-derived adult stromal cells heal critical-size mouse calvarial defects", *Nature Biotechnology*, 22:560-567 (2004).
Cui et al., "Comparison of Lumbar Spine Fusion Using Mixed and Cloned Marrow Cells", *SPIN*, 26:2305-2310 (2001).
Grundel et al., "Autogeneic Bone Marrow and Porous Biphasic Calcium Phosphate Ceramic for Segmental Bone Defects in the Canine Ulna", *Clin. Orthop. Rel. Res.*, 26:224-258 (1991).
Halvorsen et al., "Extracellular Matrix Mineralization and Osteoblast Gene Expression by Human Adipose Tissue-Derived Stromal Cells", *Tissue Engineering*, 7:729-741 (2001).
Halvorsen et al., "Thiazolidinediones and Glucocorticoids Synergistically Induce Differentiation of Human Adipose Tissue Stromal Cells: Biochemical, Cellular, and Molecular Analysis", *Metabolism*, 50:407-413 (2001).
Hickok et al., "Human Adipose-Derived Adult Stem Cells Produce Osteoid in Vivo", *Tissue Engineering*, 10:371-380 (2004).
Puissant et al., "Immunomodulatory effect of human adipose tissue-derived adult stem cells: comparison with bone marrow mesenchymal stem cells", *Br. J. Haematol.*, 129(1):118-29 (2005).
Sen et al., "Adipogenic Potential of Human Adipose Derived Stromal Cells from Multiple Donors in Heterogeneous", *J. Cell. Biochem.*, 81:312-319 (2001).
Wang et al., "Effect of Regional Gene Therapy with Bone Morphogenetic Protein-2-Producing Bone Marrow Cells on Spinal Fusion in Rats", *J. Bone and Joint Surgery*, 85A:905-911 (2003).
Werntz et al., "Qualitative and Quantitative Analysis of Orthotopic Bone Regeneration by Marrow", *J. Orthop. Res.*, 14:85-93 (1996).
Wolff et al., "Histomorphometric Analysis of the Repair of a Segmental Diaphyseal Defect with Ceramic and Titanium Fibermetal Implants: Effects of Bone Marrow", *J. Orthop. Res.*, 12:439-446 (1994).

* cited by examiner

*Primary Examiner* — Taeyoon Kim
(74) *Attorney, Agent, or Firm* — DLA Piper LLP (US)

(57) ABSTRACT

The present invention encompasses methods and compositions for treating a bone condition. The isolated adipose tissue-derived stromal cell of the invention and products related thereto have a plethora of uses, including but not limited to research, diagnostic, and therapeutic applications such as in spinal fusion procedures.

25 Claims, 5 Drawing Sheets

USE OF ADIPOSE TISSUE-DERIVED STROMAL CELLS IN SPINAL FUSION

CROSS-REFERENCE TO RELATED APPLICATIONS

This application is a continuation of U.S. patent application Ser. No. 11/194,270, filed Aug. 1, 2005 (now abandoned), where this application is incorporated herein by reference in its entirety.

BACKGROUND OF THE INVENTION

There generally are two types of bone conditions: 1) non-metabolic bone conditions, such as bone fractures, bone/spinal deformation, osteosarcoma, myeloma, bone dysplasia and scoliosis, and 2) metabolic bone conditions, such as osteoporosis, osteomalacia, rickets, fibrous osteitis, renal bone dystrophy and Paget's disease of bone. Osteoporosis, a metabolic bone condition, is a systemic disease characterized by increased bone fragility and fracturability due to decreased bone mass and change in fine bone tissue structure, its major clinical symptoms including spinal kyphosis, and fractures of dorsolumbar bones, vertebral centra, femoral necks, lower end of radius, ribs, upper end of humerus, and others. In bone tissue, bone formation and destruction due to bone resorption occur constantly. Upon deterioration of the balance between bone formation and bone destruction due to bone resorption, a quantitative reduction in bone occurs. Traditionally, bone resorption suppressors such as estrogens, calcitonin and bis-phosphonates have been mainly used to treat osteoporosis.

With respect to bone/spinal conditions, over 75% of the American population suffers from back pain sometime during their life. Underlying medical illnesses can contribute to back pain. These include scoliosis, spinal stenosis, degenerative disc disease, infectious processes, tumors, and trauma. The repair of large segmental defects in diaphyseal bone is a significant problem faced by orthopaedic surgeons today. Although such bone loss may occur as the result of acute injury, these massive defects commonly present secondary to congenital malformations, benign and malignant tumors, osseous infection, and fracture non-union. The use of fresh autologous bone graft material has been viewed as the historical standard of treatment but is associated with substantial morbidity including infection, malformation, pain, and loss of function (Kahn et al., 1995, Clin. Orthop. Rel. Res. 313: 69-75). The complications resulting from graft harvest, combined with its limited supply, have inspired the development of alternative strategies for the repair of clinically significant bone defects. The primary approach to this problem has focused on the development of effective bone implant materials.

Three general classes of bone implants have emerged from these investigational efforts, and these classes may be categorized as osteoconductive, osteoinductive, or directly osteogenic. Allograft bone is probably the best known type of osteoconductive implant. Although widely used for many years, the risk of disease transmission, host rejection, and lack of osteoinduction compromise its desirability (Leads, 1988, JAMA 260:2487-2488). Synthetic osteoconductive implants include titanium fibermetals and ceramics composed of hydroxyapatite and/or tricalcium phosphate. The favorably porous nature of these implants facilitate bony ingrowth, but their lack of osteoinductive potential limits their utility. A variety of osteoinductive compounds have also been studied, including demineralized bone matrix, which is known to contain bone morphogenic proteins (BMP). Since the original discovery of BMPs, others have characterized, cloned, expressed, and implanted purified or recombinant BMPs in orthotopic sites for the repair of large bone defects (Gerhart et al., 1993, Clin. Orthop. Rel. Res. 293:317-326; Stevenson et al., 1994, J. Bone Joint Surg. 76:1676-1687; Wozney et al., 1988 Science 242:1528-1534). The success of this approach has hinged on the presence of mesenchymal cells capable of responding to the inductive signal provided by the BMP (Lane et al., 1994, In First International Conference on Bone Morphogenic Proteins). It is these mesenchymal progenitors which undergo osteogenic differentiation and are ultimately responsible for synthesizing new bone at the surgical site.

One alternative to the osteoinductive approach is the implantation of living cells which are directly osteogenic. Since bone marrow has been shown to contain a population of cells which possess osteogenic potential, some have devised experimental therapies based on the implantation of fresh autologous or syngeneic marrow at sites in need of skeletal repair (Grundel et al., 1991, Clin. Orthop. Rel. Res. 266:244-258; Werntz et al., 1996, J. Orthop. Res. 14:85-93; Wolff et al., 1994, J. Orthop. Res. 12:439-446). Though sound in principle, the practicality of obtaining enough bone marrow with the requisite number of osteoprogenitor cells is limiting.

The emerging field of regenerative medicine seeks to combine biomaterials, growth factors, and cells as novel therapeutics to repair damaged tissues and organs. As this specialty grows, there is a demand for a reliable, safe, and effective source of human adult stem cells to serve in tissue engineering applications. For regulatory purposes, these cells must be defined by quantifiable measures of purity. For practical purposes at the clinical level, these cells should be available as an "off the shelf" product immediately available upon demand at the point of care. From a commercial standpoint, the ability to use allogeneic, as opposed to autologous, adult stem cells for transplantation would have a significant positive impact on product development. Under these circumstances, a single lot of cells derived from one donor could be transplanted to multiple mammals, reducing the costs of both quality control and quality assurance.

Studies have demonstrated the existence of adult stem cells in multiple tissue sites. Cells derived from bone marrow, known as mesenchymal stem cells (MSC) or bone marrow stromal cells (BMSC), have been extensively characterized (Castro-Malaspina et al., 1980, Blood 56:289-30125; Piersma et al., 1985, Exp. Hematol 13:237-243; Simmons et al., 1991, Blood 78:55-62; Beresford et al., 1992, J. Cell. Sci. 102:341-3 51; Liesveld et al., 1989, Blood 73:1794-1800; Liesveld et al., Exp. Hematol 19:63-70; Bennett et al., 1991, J. Cell. Sci. 99:131-139). Recent studies have demonstrated that allogeneic bone marrow-derived MSCs can be transplanted (Bartholomew et al., 2002, Exp. Hematol. 30:42-8), and used to repair a critical sized orthopedic defect in a canine model (Arinzeh et al., 2003, J. Bone Joint Surg. Am. 85-A: 1927-35). However, MSCs represent approximately 1 out of every 10,000 to 100,000 nucleated bone marrow cells or about 200 cells per ml of bone marrow aspirate (Bruder et al., 2000, Principles of Tissue Engineering, $2^{nd}$ Edition, Academic Press). In order to obtain MSC numbers sufficient for tissue engineering applications, it is necessary to expand the bone marrow-derived MSCs through multiple passages in vitro.

In contrast to bone marrow, adipose tissue is easily accessible for surgical harvest and abundant in the average adult American. Recently, it has been demonstrated that adipose tissue can serve as a source of stem cells (known as adipose derived adult stem cells or ADAS cells). These cells are capable of differentiating along multiple lineage pathways. In response to specific chemicals, hormones, and/or cytokines, human and rodent ADAS cells express biochemical and histological characteristics consistent with adipose, bone, cartilage, muscle, and neuronal cells. In a recent study, murine ADAS cells accelerated the repair a critical sized calvarial defect (Cowan et al., 2004, Nat. Biotechnol. 22:560-7).

Bone grafting is often used for the treatment of bone conditions. Indeed, more than 1.4 million bone grafting procedures are performed in the world annually. The success or failure of bone grafting is dependent upon a number of factors including the vitality of the site of the graft, the graft processing, and the immunological compatibility of the engrafted tissue. In view of the prevalence of bone conditions, there is a need for novel sources of bone for therapeutic, diagnostic, and research uses. The present invention satisfies this need.

BRIEF SUMMARY OF THE INVENTION

The invention includes a method of enhancing the fusion of bone following a spinal fusion procedure in a mammal comprising administering an isolated adipose tissue-derived adult stromal (ADAS) cell to the spine of the mammal, wherein the ADAS cell differentiates in vivo into a cell that expresses at least one characteristic of a bone cell.

The invention also includes a method of performing one or more spinal fusions in a mammal comprising administering an ADAS cell to the spine of the mammal to facilitate a single or multi level spinal fusion. Preferably, following administration of the ADAS into the spine of the mammal, the ADAS cell differentiates in vivo into a cell that expresses at least one characteristic of a bone cell.

In one aspect the ADAS cell is cultured in vitro for a period of time without being induced to differentiate prior to the administration of the cell to the mammal.

In another aspect, the ADAS cell is allogeneic with respect to the mammal.

In yet another aspect, the ADAS cell induces bone formation for intervertebral body spinal fusion.

In another aspect, the ADAS cell induces bone formation for intertransverse process spinal fusion.

In one aspect, the ADAS cell further comprises a biocompatible matrix. Preferably, the biocompatible matrix is selected from the group consisting of calcium alginate, agarose, fibrin, collagen, laminin, fibronectin, glycosaminoglycan, hyaluronic acid, heparin sulfate, chondroitin sulfate A, dermatan sulfate, and bone matrix gelatin.

In another aspect, the ADAS cell is genetically modified.

In yet another aspect, the ADAS cell is administered into one or more interbody spaces in the spine of the mammal.

In a further aspect, the spinal fusion is in a segment of the spine selected from the group consisting of cervical, thoracic, lumbar, lumbosacral and sacro-iliac (SI) joint.

In yet a further aspect, the ADAS cell is administered into one or more interbody spaces by an approach selected from the group consisting of a posterior approach, a posterolateral approach, an anterior approach, an anterolateral approach, and a lateral approach.

In yet another aspect, the mammal is a human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A depicts the intervertebral space in the lumbar spine. FIGS. 1B and 1C demonstrates introduction of a mechanical device and bone grafts to stabilize the space, respectively. FIG. 1D is an image depicting the spine.

DETAILED DESCRIPTION

Figure 1:
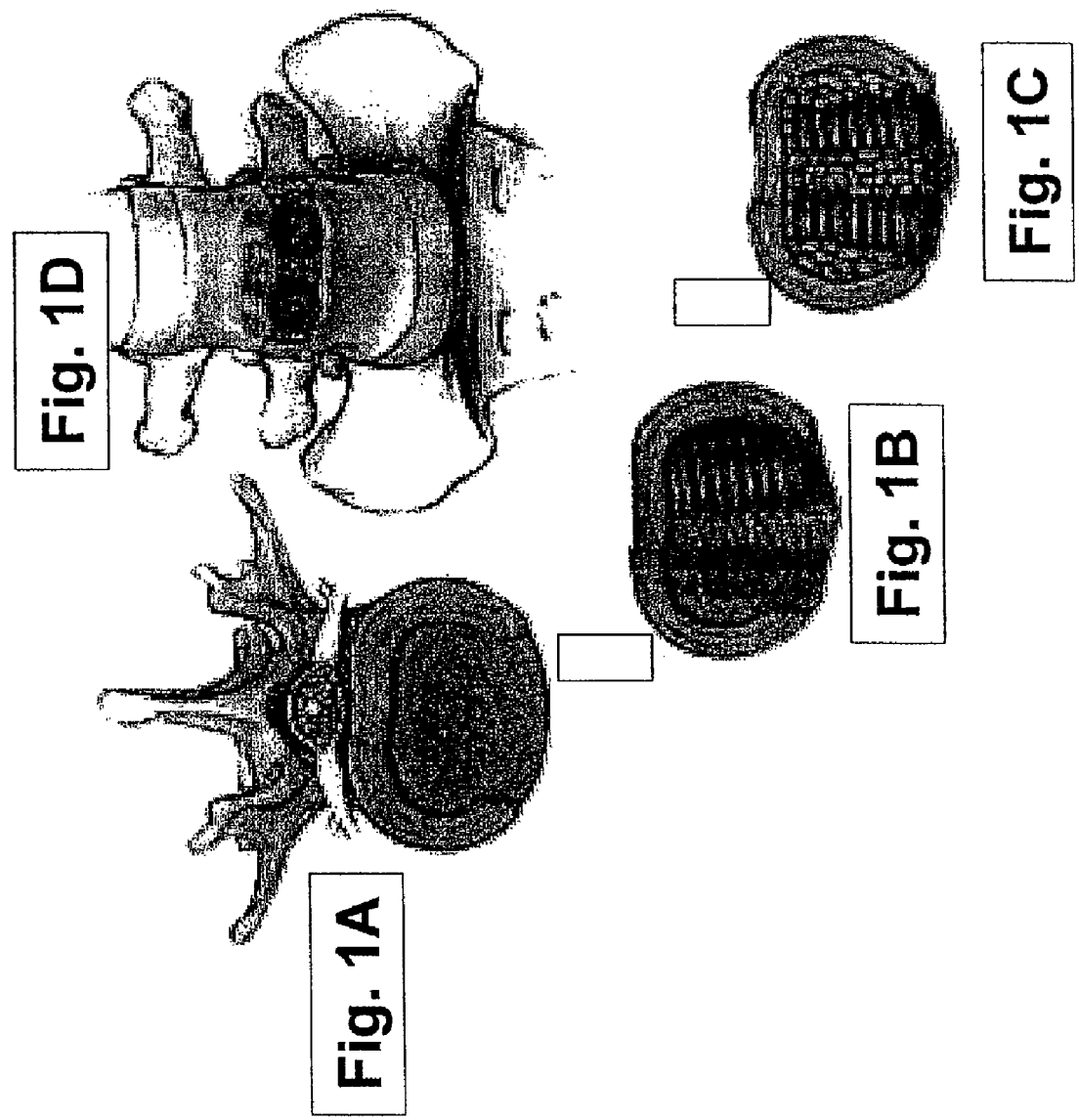
FIG. 1 is an image depicting a spinal fusion procedure.

The present invention encompasses methods and compositions for treating a bone disease. In a preferred embodiment, an isolated adipose tissue-derived adult stromal (ADAS) cell of the invention is used to enhance the fusion of bone following a spinal fusion procedure in a mammal.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

The term "adipose tissue-derived cell" refers to a cell that originates from adipose tissue. The initial cell population isolated from adipose tissue is a heterogeneous cell population including, but not limited to stromal vascular fraction (SVF) cells.

As used herein, the term "adipose derived stromal cells," "adipose tissue-derived stromal cells," "adipose tissue-derived adult stromal (ADAS) cells," or "adipose-derived stem cells (ASCs)" are used interchangeably and refer to stromal cells that originate from adipose tissue which can serve as stem cell-like precursors to a variety of different cell types such as but not limited to adipocytes, osteocytes, chondrocytes, muscle and neuronal/glial cell lineages.

"Adipose" refers to any fat tissue. The adipose tissue may be brown or white adipose tissue. Preferably, the adipose tissue is subcutaneous white adipose tissue. Such cells may comprise a primary cell culture or an immortalized cell line. The adipose tissue may be from any organism having fat tissue. Preferably the adipose tissue is mammalian, most preferably the adipose tissue is human. A convenient source of human adipose tissue is that derived from liposuction surgery. However, the source of adipose tissue or the method of isolation of adipose tissue is not critical to the invention.

"Allogeneic" refers to a graft derived from a different animal of the same species.

As used herein, the term "autologous" is meant to refer to any material derived from the same individual to which it is later to be re-introduced into the individual.

"Xenogeneic" refers to a graft derived from a mammal of a different species.

As used herein, the term "biocompatible lattice," is meant to refer to a substrate that can facilitate formation into three-dimensional structures conducive for tissue development. Thus, for example, cells can be cultured or seeded onto such a biocompatible lattice, such as one that includes extracellular matrix material, synthetic polymers, cytokines, growth factors, etc. The lattice can be molded into desired shapes for facilitating the development of tissue types. Also, at least at an early stage during culturing of the cells, the medium and/or substrate is supplemented with factors (e.g., growth factors, cytokines, extracellular matrix material, etc.) that facilitate the development of appropriate tissue types and structures.

As used herein, the term "bone condition (or injury or disease)" refers to disorders or diseases of the bone including, but is not limited to, acute, chronic, metabolic and non-metabolic conditions of the bone. The term encompasses conditions caused by disease, trauma or failure of the tissue to develop normally. Examples of bone conditions include, but are not limited, a bone fracture, a bone/spinal deformation, osteosarcoma, myeloma, bone dysplasia, scoliosis, osteoporosis, osteomalacia, rickets, fibrous osteitis, renal bone dystrophy, and Paget's disease of bone.

"Differentiation medium" is used herein to refer to a cell growth medium comprising an additive or a lack of an additive such that a stem cell, adipose derived adult stromal cell or other such progenitor cell, that is not fully differentiated when incubated in the medium, develops into a cell with some or all of the characteristics of a differentiated cell.

"Expandability" is used herein to refer to the capacity of a cell to proliferate, for example, to expand in number or in the case of a cell population to undergo population doublings.

"Graft" refers to a cell, tissue, organ or otherwise any biological compatible lattice for transplantation.

By "growth factors" is intended the following specific factors including, but not limited to, growth hormone, erythropoietin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor (EGF), fibroblast growth factor (FGF), nerve growth factor, ciliary neurotrophic factor, platelet derived growth factor (PDGF), and bone morphogenetic protein at concentrations of between picogram/ml to milligram/ml levels.

As used herein, the term "growth medium" is meant to refer to a culture medium that promotes growth of cells. A growth medium will generally contain animal serum. In some instances, the growth medium may not contain animal serum.

An "isolated cell" refers to a cell which has been separated from other components and/or cells which naturally accompany the isolated cell in a tissue or mammal.

As used herein, the term "multipotential" or "multipotentiality" is meant to refer to the capability of a stem cell of the central nervous system to differentiate into more than one type of cell.

As used herein, the term "modulate" is meant to refer to any change in biological state, i.e. increasing, decreasing, and the like.

As used herein, the term "non-immunogenic" is meant to refer to the discovery that ADAS cells do not induce proliferation of T cells in an MLR. However, non-immunogenic should not be limited to T cell proliferation in an MLR, but rather should also apply to ADAS cells not inducing T cell proliferation in vivo.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

"Progression of or through the cell cycle" is used herein to refer to the process by which a cell prepares for and/or enters mitosis and/or meiosis. Progression through the cell cycle includes progression through the G1 phase, the S phase, the G2 phase, and the M-phase.

The terms "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. Unlike pluripotent stem cells, lineage-committed progenitor cells are generally considered to be incapable of giving rise to numerous cell types that phenotypically differ from each other. Instead, progenitor cells give rise to one or possibly two lineage-committed cell types.

The term "stromal cell medium" as used herein, refers to a medium useful for culturing ADAS cells. A non-limiting example of a stromal cell medium is a medium comprising DMEM/F 12 Ham's, 10% fetal bovine serum, 100 U penicillin/100 µg streptomycin/0.25 µg Fungizone. Typically, the stromal cell medium comprises a base medium, serum and an antibiotic/antimycotic. However, ADAS cells can be cultured with stromal cell medium without an antibiotic/antimycotic and supplemented with at least one growth factor. Preferably the growth factor is human epidermal growth factor (hEGF). The preferred concentration of hEGF is about 1-50 ng/ml, more preferably the concentration is about 5 ng/ml. The preferred base medium is DMEM/F12 (1:1). The preferred serum is fetal bovine serum (FBS) but other sera may be used including horse serum or human serum. Preferably up to 20% FBS will be added to the above media in order to support the growth of stromal cells. However, a defined medium could be used if the necessary growth factors, cytokines, and hormones in FBS for stromal cell growth are identified and provided at appropriate concentrations in the growth medium. It is further recognized that additional components may be added to the culture medium. Such components include but are not limited to antibiotics, antimycotics, albumin, growth factors, amino acids, and other components known to the art for the culture of cells. Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml. However, the invention should in no way be construed to be limited to any one medium for culturing stromal cells. Rather, any media capable of supporting stromal cells in tissue culture may be used.

The term "pharmaceutically acceptable carrier (or medium)" which may be used interchangeably with the term biologically compatible carrier or medium, refers to reagents, cells, compounds, materials, compositions, and/or dosage forms which are, within the scope of being suitable for use in contact with the tissues of human beings and animals without excessive toxicity, irritation, allergic response, or other complication commensurate with a reasonable benefit/risk ratio.

A "suitable interbody space" as the term is used herein means the space between adjacent vertebrae where a disc resides in a healthy spine but which is either at least partially devoid of disc material due to wear and tear on the vertebral column or has been prepared using techniques known in the art to surgically create a void in the disc space.

As used herein, a "therapeutically effective amount" is the amount of ADAS cells sufficient to provide a beneficial effect to the subject to which the cells are administered.

"Treating (or treatment of)" refers to ameliorating the effects of, or delaying, halting or reversing the progress of, or delaying or preventing the onset of, a bone condition.

As used herein "endogenous" refers to any material from or produced inside an organism, cell or system.

"Exogenous" refers to any material introduced from or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The phrase "under transcriptional control" or "operatively linked" as used herein means that the promoter is in the correct location and orientation in relation to the polynucleotides to control RNA polymerase initiation and expression of the polynucleotides.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (i.e., naked or contained in liposomes) and viruses that incorporate the recombinant polynucleotide.

Description

The present invention relates to the discovery that adipose tissue-derived adult stromal (ADAS) cells can differentiate into a variety of different cell types including, but not limited to, adipocytes, osteocytes, chondrocytes, muscle and neuronal/glial cell lineages. Particularly, the invention relates to the observation that ADAS cells can differentiate along the osteogenic lineage in vivo.

Based on the present disclosure, an ADAS cell can be successfully used in cell and/or gene therapy for experimental/therapeutic purposes. For example, the cells can be used in the treatment of bone diseases. Preferably, the cells are used to enhance the fusion of bone following a spinal fusion procedure. Spinal fusion is a common orthopedic and neurosurgical procedure used to treat back pain in mammals suffering from degenerative disc disease, spinal stenosis, scoliosis, spinal fracture, tumor, and the like.

Isolation and Culturing of ADAS

The ADAS cells useful in the methods of the present invention may be isolated by a variety of methods known to those skilled in the art. For example, such methods are described in U.S. Pat. No. 6,153,432, which is incorporated herein in its entirety. In a preferred method, ADAS cells are isolated from a mammalian subject, preferably a human subject. In humans, the ADAS cells are typically isolated from liposuction material. If the cells of the invention are to be transplanted into a human subject, it is preferable that the ADAS cells be isolated from that same subject so as to provide for an autologous transplant.

In another aspect of the invention, the administered ADAS cells may be allogeneic with respect to the recipient. The allogeneic ADAS cells are isolated from a donor that is a different individual of the same species as the recipient. Following isolation, the cells are cultured using the methods disclosed herein to produce an allogeneic product. The invention also encompasses ADAS cells that are xenogeneic with respect to the recipient.

Without limiting the invention in anyway, stromal cells from adipose tissue can be isolated using the methods disclosed herein. Briefly, human adipose tissue from subcutaneous depots are removed by liposuction surgery. The adipose tissue is then transferred from the liposuction cup into a 500 ml sterile beaker and allowed to settle for about 10 minutes. Precipitated blood is removed by suction. About a 125 ml volume (or less) of the tissue is transferred to a 250 ml centrifuge tube, and the tube is then filled with Krebs-Ringer Buffer. The tissue and buffer are allowed to settle for about three minutes or until a clear separation is achieved, and then the buffer is removed by aspiration. The tissue can be washed with Krebs-Ringer Buffer for an additional four to five times or until the tissue becomes orange-yellow in color and until the buffer becomes light tan in color.

The stromal cell of the adipose tissue can be dissociated using collagenase treatment. Briefly, the buffer is removed from the tissue and replaced with about 2 mg collagenase/ml Krebs Buffer (Worthington, Me.) solution at a ratio of 1 ml collagenase solution/ml tissue. The tubes are incubated in a 37° C. water bath with intermittent shaking for about 30 to 35 minutes.

Stromal cells are isolated from other components of the adipose tissue by centrifugation for 5 minutes at 500×g at room temperature. The oil and adipocyte layer are removed by aspiration. The remaining fraction can be resuspended in approximately 100 ml of phosphate buffered saline (PBS) by vigorous swirling, divided into 50 ml tubes and centrifuged for five minutes at 500×g. The buffer is removed by aspiration, leaving the stromal cells. The stromal cells are then resuspended in stromal cell medium, and plated at an appropriate cell density and incubated at 37° C. in 5% $CO_2$ overnight. Once attached to the tissue culture dish or flask, the cultured stromal cells can be used immediately or maintained in culture for a period of time or a number of passages before using the cells according to the methods disclosed herein. However, the invention should in no way be construed to be limited to any one method of isolating stromal cells. Rather, any method of isolating ADAS cells should be encompassed in the present invention.

Any medium capable of supporting fibroblasts in cell culture may be used to culture ADAS. Media formulations that support the growth of fibroblasts include, but are not limited to, Minimum Essential Medium Eagle, ADC-1, LPM (bovine serum albumin-free), F10 (HAM), F12 (HAM), DCCM1, DCCM2, RPMI 1640, BGJ Medium (with and without Fitton-Jackson Modification), Basal Medium Eagle (BME-with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E-with Earle's salt base), Medium M199 (M199H-with Hank's salt base), Minimum Essential Medium Eagle (MEM-E-with Earle's salt base), Minimum Essential Medium Eagle (MEM-H-with Hank's salt base) and Minimum Essential Medium Eagle (MEM-NAA with non-essential amino acids), and the like. A preferred medium for culturing ADAS is DMEM, more preferably DMEM/F12 (1:1).

Additional non-limiting examples of media useful in the methods of the invention can contain fetal serum of bovine or other species at a concentration at least 1% to about 30%, preferably at least about 5% to 15%, most preferably about 10%. Embryonic extract of chicken or other species can be present at a concentration of about 1% to 30%, preferably at least about 5% to 15%, most preferably about 10%.

Following isolation, ADAS cells are incubated in stromal cell medium in a culture apparatus for a period of time or until the cells reach confluency before passing the cells to another culture apparatus. The culturing apparatus can be of any culture apparatus commonly used in culturing cells in vitro. Preferably, the level of confluence is greater than 70% before passing the cells to another culture apparatus. More preferably, the level of confluence is greater than 90%. A period of time can be any time suitable for the culture of cells in vitro. Stromal cell medium may be replaced during the culture of the ADAS cells at any time. Preferably, the stromal cell medium is replaced every 3 to 4 days. ADAS cells are then harvested from the culture apparatus whereupon the ADAS cells can be used immediately or cryopreserved to be stored for use at a later time. ADAS cells may be harvested by trypsinization, EDTA treatment, or any other procedure used to harvest cells from a culture apparatus.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

Genetic Modification

The cells of the present invention can also be used to express a foreign protein or molecule for a therapeutic purpose or in a method of tracking the assimilation of the cell and/or its differentiation in the recipient. Thus, the invention encompasses expression vectors and methods for the introduction of exogenous DNA into ADAS cells with concomitant expression of the exogenous DNA in the ADAS cells. Methods for introducing and expressing DNA in a cell are well known to the skilled artisan and include those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The isolated nucleic acid can encode a molecule used to track the migration, assimilation, and survival of ADAS cells once they are introduced in the recipient. Proteins useful for tracking a cell include, but are not limited to, green fluorescent protein (GFP), any of the other fluorescent proteins (e.g., enhanced green, cyan, yellow, blue and red fluorescent proteins; Clontech, Palo Alto, Calif.), or other tag proteins (e.g., LacZ, FLAG-tag, Myc, His$_6$, and the like).

Tracking the migration, assimilation and/or differentiation of an ADAS cell of the present invention is not limited to the use of detectable molecules expressed by a vector or virus. The migration, assimilation, and/or differentiation of a cell can also be assessed using a series of probes that facilitate localization of transplanted ADAS cells within a mammal. Tracking an ADAS cell transplant may further be accomplished using antibodies or nucleic acid probes for cell-specific markers detailed elsewhere herein.

The term "genetic modification" as used herein refers to the stable or transient alteration of the genotype of an ADAS cell by intentional introduction of exogenous DNA. DNA may be synthetic, or naturally derived, and may contain genes, portions of genes, or other useful DNA sequences. The term "genetic modification" as used herein is not meant to include naturally occurring alterations such as that which occurs through natural viral activity, natural genetic recombination, or the like.

Exogenous DNA may be introduced to an ADAS cell using viral vectors (retrovirus, modified herpes viral, herpes-viral, adenovirus, adeno-associated virus, lentiviral, and the like) or by direct DNA transfection (lipofection, calcium phosphate transfection, DEAE-dextran, electroporation, and the like).

When the purpose of genetic modification of the cell is for the production of a biologically active substance, the substance will generally be one that is useful for the treatment of a given disorder. For example, it may be desired to genetically modify cells so that they secrete a certain growth factor product associated with bone formation.

The cells of the present invention can be genetically modified by having exogenous genetic material introduced into the cells, to produce a molecule such as a trophic factor, a growth factor, a cytokine, and the like, which is beneficial to culturing the cells. In addition, by having the cells genetically modified to produce such a molecule, the cell can provide an additional therapeutic effect to the mammal when transplanted into a mammal in need thereof. For example, the genetically modified cell can secrete a molecule that is beneficial neighboring cells in the mammal.

As used herein, the term "growth factor product" refers to a protein, peptide, mitogen, or other molecule having a growth, proliferative, differentiative, or trophic effect on a cell. For example, growth factor products useful in the treatment of bone disorders include, but are not limited to, FGF, TGF-β, insulin-like growth factor, and bone morphogenetic protein.

According to the present invention, gene constructs which comprise nucleotide sequences that encode heterologous proteins are introduced into the ADAS cells. That is, the cells are genetically altered to introduce a gene whose expression has therapeutic effect in the mammal. According to some aspects of the invention, ADAS cells from the mammal to be treated or from another mammal, may be genetically altered to replace a defective gene and/or to introduce a gene whose expression has therapeutic effect in the mammal being treated.

In all cases in which a gene construct is transfected into a cell, the heterologous gene is operably linked to regulatory sequences required to achieve expression of the gene in the cell. Such regulatory sequences typically include a promoter and a polyadenylation signal.

The gene construct is preferably provided as an expression vector that includes the coding sequence for a heterologous protein operably linked to essential regulatory sequences such that when the vector is transfected into the cell, the coding sequence will be expressed by the cell. The coding sequence is operably linked to the regulatory elements necessary for expression of that sequence in the cells. The nucleotide sequence that encodes the protein may be cDNA, genomic DNA, synthesized DNA or a hybrid thereof or an RNA molecule such as mRNA.

The gene construct includes the nucleotide sequence encoding the beneficial protein operably linked to the regulatory elements and may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The regulatory elements for gene expression include: a promoter, an initiation codon, a stop codon, and a polyadenylation signal. It is preferred that these elements be operable in the cells of the present invention. Moreover, it is preferred that these elements be operably linked to the nucleotide sequence that encodes the protein such that the nucleotide sequence can be expressed in the cells and thus the protein can be produced. Initiation codons and stop codons are generally considered to be part of a nucleotide sequence that encodes the protein. However, it is preferred that these elements are functional in the cells. Similarly, promoters and polyadenylation signals used must be functional within the cells of the present invention. Examples of promoters useful to practice the present invention include but are not limited to promoters that are active in many cells such as the cytomegalovirus promoter, SV40 promoters and retroviral promoters. Other examples of promoters useful to practice the present invention include but are not limited to tissue-specific promoters, i.e. promoters that function in some tissues but not in others; also, promoters of genes normally expressed in the cells with or without specific or general enhancer sequences. In some embodiments, promoters are used which constitutively express genes in the cells with or without enhancer sequences. Enhancer sequences are provided in such embodiments when appropriate or desirable.

The cells of the present invention can be transfected using well known techniques readily available to those having ordinary skill in the art. Exogenous genes may be introduced into the cells using standard methods where the cell expresses the protein encoded by the gene. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, recombinant adenovirus vectors are used to introduce DNA with desired sequences into the cell. In some embodiments, recombinant retrovirus vectors are used to introduce DNA with desired sequences into the cells. In some embodiments, standard CaPO$_4$, DEAE dextran or lipid carrier mediated transfection techniques are employed to incorporate desired DNA into dividing cells. Standard antibiotic resistance selection techniques can be used to identify and select transfected cells. In some embodiments, DNA is introduced directly into cells by microinjection. Similarly, well-known electroporation or particle bombardment techniques can be used to introduce foreign DNA into the cells. A second gene is usually co-transfected or linked to the therapeutic gene. The second gene is frequently a selectable antibiotic-resistance gene. Transfected cells can be selected by growing the cells in an antibiotic that will kill cells that do not take up the selectable gene. In most cases where the two genes are unlinked and co-transfected, the cells that survive the antibiotic treatment have both genes in them and express both of them.

It should be understood that the methods described herein may be carried out in a number of ways and with various modifications and permutations thereof that are well known in the art. It may also be appreciated that any theories set forth as to modes of action or interactions between cell types should not be construed as limiting this invention in any manner, but are presented such that the methods of the invention can be more fully understood.

Therapeutic Use of ADAS Cells

In addition to the fact that ADAS cells can differentiate along different cell lineages, the invention also relates to the discovery that ADAS cells lack immunogenic characteristics with respect to inducing proliferation of T cells. This characteristic is an indication that there is a reduced likelihood of an immune rejection by the recipient's immune cells. In addition, ADAS cells have been shown not to stimulate allogeneic PBMCs in a mixed lymphocyte reaction.

In some embodiments of the invention, it may not be necessary or desirable to immunosuppress a mammal prior to initiation of cell/gene therapy with ADAS cells. Accordingly, transplantation with allogeneic, or even xenogeneic, ADAS cells is included in the invention.

The use of ADAS cells for the treatment of a disease, disorder, or a condition of the bone provides an additional advantage in that the ADAS cells can be introduced into a recipient without the requirement of an immunosuppressive agent. Successful transplantation of a cell is believed to require the permanent engraftment of the donor cell without inducing a graft rejection immune response generated by the recipient. Typically, in order to prevent a graft rejection response, nonspecific immunosuppressive agents such as cyclosporine, methotrexate, steroids and FK506 are used. These agents are administered on a daily basis and if administration is stopped, graft rejection usually results. However, an undesirable consequence in using nonspecific immunosuppressive agents is that they function by suppressing all aspects of the immune response (general immune suppression), thereby greatly increasing a recipient's susceptibility to infection and other diseases.

The present invention provides a method of treating a disease, disorder, or a condition of the bone by introducing undifferentiated or differentiated ADAS cells into the recipient without the requirement of immunosuppressive agents. There is therefore a reduced susceptibility for the recipient of the transplanted ADAS cell to incur infection and other diseases, including cancer relating conditions that is associated with immunosuppression therapy.

The present invention includes the administration of an allogeneic or a xenogeneic ADAS cell, or otherwise an ADAS cell that is genetically disparate from the recipient, into a recipient to provide a benefit to the recipient. The present invention provides a method of using ADAS cells to treat a disease, disorder or condition of the bone without the requirement of using immunosuppressive agents when administering the cells to a recipient.

In a further embodiment, the ADAS cell used in the present invention can be isolated, from adipose tissue of any species of mammal, including but is not limited to, human, mouse, rat, ape, gibbon, bovine. Preferably, the ADAS cell is isolated from a human, a mouse, or a rat. More preferably, the ADAS cell is isolated from a human.

The ADAS cell may be administered to a mammal following a period of in vitro culturing. The ADAS cell may be cultured in a manner that induces the ADAS cell to differentiate in vitro. However, it is preferred that the ADAS cell is implanted into the recipient in an undifferentiated state and that the implanted ADAS cell differentiates to express at least one characteristic of a bone cell in vivo.

The ADAS cells of this invention can be transplanted into a mammal using techniques known in the art such as i.e., those described in U.S. Pat. Nos. 5,082,670 and 5,618,531, each incorporated herein by reference, or into any other suitable site in the body. Transplantation of the cells of the present invention can be accomplished using techniques well known in the art as well as those described herein or as developed in the future. The present invention comprises a method for transplanting, grafting, infusing, or otherwise introducing the cells into a mammal, preferably, a human.

The number of ADAS cells administered to a mammal may be related to, for example, the cell yield after adipose tissue processing. A portion of the total number of cells may be retained for later use or cyropreserved. In addition, the dose delivered depends on the route of delivery of the cells to the mammal.

The dosage of the ADAS cells varies within wide limits and may be adjusted to the individual requirements in each particular case. The number of cells used depends on the weight and condition of the recipient, the number and/or frequency of administrations, and other variables known to those of skill in the art. This number can be adjusted by orders of magnitude to achieve the desired therapeutic effect.

Between about $10^5$ and about $10^{13}$ ADAS cells per 100 kg body weight can be administered to the individual. In some embodiments, between about $1.5 \times 10^6$ and about $1.5 \times 10^{12}$ cells are administered per 100 kg body weight. In some embodiments, between about $1 \times 10^9$ and about $5 \times 10^{11}$ cells are administered per 100 kg body weight. In other embodiments, between about $4 \times 10^9$ and about $2 \times 10^{11}$ cells are administered per 100 kg body weight. In yet other embodiments, between about $5 \times 10^8$ cells and about $1 \times 10^{10}$ cells are administered per 100 kg body weight.

ADAS cells can be suspended in an appropriate diluent, at a concentration of from about 0.01 to about $5 \times 10^6$ cells/ml. Suitable excipients for injection solutions are those that are biologically and physiologically compatible with the ADAS cells and with the recipient, such as buffered saline solution or other suitable excipients. The composition for administration can be formulated, produced and stored according to standard methods complying with proper sterility and stability.

The cells may also be encapsulated and used to deliver biologically active molecules, according to known encapsulation technologies, including microencapsulation (see, e.g., U.S. Pat Nos. 4,352,883; 4,353,888; and 5,084,350, herein incorporated by reference), or macroencapsulation (see, e.g., U.S. Pat. Nos. 5,284,761; 5,158,881; 4,976,859; and 4,968,733; and International Publication Nos. WO 92/19195; WO 95/05452, all of which are incorporated herein by reference). For macroencapsulation, cell number in the devices can be varied; preferably, each device contains between $10^3$-$10^9$ cells, most preferably, about $10^5$ to $10^7$ cells. Several macroencapsulation devices may be implanted in the mammal. Methods for the macroencapsulation and implantation of cells are well known in the art and are described in, for example, U.S. Pat. No. 6,498,018.

The mode of administration of the cells of the invention to the mammal may vary depending on several factors including the type of disease being treated, the age of the mammal, whether the cells are differentiated or not, whether the cells have heterologous DNA introduced therein, and the like. The cells may be introduced to the desired site by direct injection, or by any other means used in the art for the introduction of compounds administered to a mammal suffering from a particular disease or disorder of the bone.

The ADAS cells can be administered into a host in a wide variety of ways. Modes of administration include, but are not limited to, intravascular, intracerebral, parenteral, intraperitoneal, intravenous, epidural, intraspinal, intrasternal, intra-articular, intra-synovial, intrathecal, intra-arterial, intracardiac, or intramuscular. Preferably, the cells are used in spinal fusion procedures.

Composition

The invention also provides a matrix for implantation into a mammal, wherein the matrix comprises an ADAS cell of the invention. The matrix can also include, but is not limited to, an ADAS cell, an ADAS cell lysate, an ADAS cell conditioned medium, and an extracellular matrix produced by an ADAS cell.

The matrix may also contain or be treated with one or more bioactive factor including, but not limited to an anti-apoptotic agent (i.e., erythropoietin, thrombopoietin, insulin-like growth factor I and insulin-like growth factor II, hepatocyte growth factor, caspase inhibitors); an anti-inflammatory agent (i.e., p38 MAPK inhibitors, TGF-beta inhibitors, statins, IL-6 and IL-1 inhibitors, and non-steroidal anti-inflammatory drugs); an immunosupressive/immunomodulatory agent; an mTOR inhibitor; an anti-proliferative agent; a corticosteroid (i.e., prednisolone, hydrocortisone); an anti-thrombogenic agent; and an anti-oxidant. The presence of a bioactive factor can contribute to the proliferation and/or differentiation of the ADAS cells.

The invention further provides in some aspects methods of regenerating bone tissue in a mammal in need thereof by administering a composition comprising an ADAS cell, a matrix, an ADAS cell lysate, an ADAS-product of the invention (i.e. molecules secreted by the ADAS cell), or any combination thereof in a mammal. As such, the invention encompasses a pharmaceutical composition, wherein the composition may be used in the treatment of a bone condition. For example, the bone condition includes, but is not limited to, a bone fracture, a bone/spinal deformation, osteosarcoma, myeloma, bone dysplasia, scoliosis, osteoporosis, osteomalacia, rickets, fibrous osteitis, renal bone dystrophy, and Paget's disease of bone. Preferably, the invention provides compositions and methods for enhancing fusion of bone following a spinal fusion procedure.

In a non-limiting embodiment, a formulation comprising the cells of the invention is prepared for administration directly to the site where the production of new bone tissue is desired. For example, the cells of the invention may be suspended in a hydrogel solution for injection. Alternatively, the hydrogel solution containing the cells may be allowed to harden, for instance in a mold, to form a matrix having cells dispersed therein prior to implantation, or once the matrix has hardened, the cell formations may be cultured so that the cells are mitotically expanded prior to implantation. The hydrogel is an organic polymer (natural or synthetic) which is cross-linked via covalent, ionic, or hydrogen bonds to create a three-dimensional open-lattice structure which entraps water molecules to form a gel. Examples of materials which can be used to form a hydrogel include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively.

In some embodiments, the polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Other examples of polymers include, but are not limited to poly-alpha-hydroxy esters, polydioxanone, propylene fumarate, poly-ethylene glycol, poly-erthoesters, polyanhydrides and polyurethanes, poly-L-lactic acid, poly-glycolic acid, and poly-lactic-co-glycolic acid.

Transplantation of ADAS Cells Using Scaffolds

The cells of the invention can be seeded onto or into a three-dimensional scaffold and implanted in vivo, where the seeded cells proliferate on the framework and form a replacement tissue in vivo in cooperation with the cells of the mammal.

In some aspects of the invention, the scaffold comprises extracellular matrix, cell lysate (e.g., soluble cell fractions), or combinations thereof, of the ADAS cells. In some embodiments, the scaffold comprises an extracellular matrix protein secreted by the cells of the invention. Alternatively, the extracellular matrix is an exogenous material selected from the group consisting of calcium alginate, agarose, fibrin, collagen, laminin, fibronectin, glycosaminoglycan, hyaluronic acid, heparin sulfate, chondroitin sulfate A, dermatan sulfate, and bone matrix gelatin. In some aspects, the matrix comprises natural or synthetic polymers.

The invention includes biocompatible scaffolds, lattices, self-assembling structures and the like, whether biodegradable or not, liquid or solid. Such Scaffolds are known in the arts of cell-based therapy, surgical repair, tissue engineering, and wound healing. Preferably the scaffolds are pretreated (e.g., seeded, inoculated, contacted with) with the cells, extracellular matrix, conditioned medium, cell lysate, or combination thereof. In some aspects of the invention, the cells adhere to the scaffold. The seeded scaffold can be introduced into a mammal's body in anyway known in the art, including but not limited to implantation, injection, surgical attachment, transplantation with other tissue, injection, and the like. The scaffold of the invention may be configured to the shape and/or size of a tissue or organ in vivo. For example, but not by way of limitation, the scaffold may be designed such that the scaffold structure supports the seeded cells without subsequent degradation; supports the cells from the time of seeding until the tissue transplant is remodeled by the host tissue;

and allows the seeded cells to attach, proliferate, and develop into a tissue structure having sufficient mechanical integrity to support itself.

Scaffolds of the invention can be administered in combination with any one or more growth factors, cells, drugs or other components described elsewhere herein that stimulate tissue formation or otherwise enhance or improve the practice of the invention. The ADAS cells to be seeded onto the scaffolds may be genetically engineered to express growth factors or drugs.

In another preferred embodiment, the cells of the invention are seeded onto a scaffold where the material exhibits specified physical properties of porosity and biomechanical strength to mimic the features of true bone, thereby promoting stability of the final structure and access and egress of metabolites and cellular nutrients. That is, the material should provide structural support and can form a scaffolding into which host vascularization and cell migration can occur. In the preferred embodiment, ADAS cells are first mixed with a carrier material before application to a scaffold. Suitable carriers include, but are not limited to, calcium alginate, agarose, types I, II, IV or other collagen isoform, fibrin, poly-lactic/poly-glycolic acid, hyaluronate derivatives, gelatin, laminin, fibronectin, starch, polysaccharides, saccharides, proteoglycans, synthetic polymers, calcium phosphate, and ceramics (i.e. hydroxyapatite, tricalcium phosphate).

The external surfaces of the three-dimensional framework may be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, and agarose.

In some embodiments, it is important to re-create in culture the cellular microenvironment found in vivo, such that the extent to which the cells of the invention are grown prior to implantation in vivo. In addition, growth factors, osteogenic inducing agents, and angiogenic factors may be added to the culture medium prior to, during, or subsequent to inoculation of the cells to trigger differentiation and tissue formation by the ADAS cells following implantation into the mammal.

Therapeutic Applications of ADAS Cells

The present invention encompasses methods for administering an ADAS cell to a mammal, including a human, in order to treat a disease where the introduction of the ADAS cells provide a therapeutic relief. The cells of the invention may be administered alone or as admixtures with other cells and/or a bioactive factor as discussed elsewhere herein. A cell that may be administered in conjunction with ADAS cells of the invention include, but is not limited to, other multipotent or pluripotent cells, an osteocyte, an osteoblast, an osteoclast, a bone lining cell, a stem cell, and a bone marrow cell. The different types of cells may be admixed with the ADAS cells immediately or shortly prior to administration to a mammal, or they may be co-cultured together for a period of time prior to administration to a mammal.

The skilled artisan will readily understand that ADAS cells can be transplanted into a mammal whereby upon receiving signals and cues from the surrounding milieu, the cells differentiate into mature cells in vivo dictated by the neighboring cellular milieu. Preferably, the ADAS cells differentiate into a cell that exhibits at least one characteristic of a bone cell. Alternatively, the ADAS cells can be differentiated in vitro into a desired cell type and the differentiated cell can be administered to a mammal in need thereof.

The invention also encompasses grafting ADAS cells in combination with other therapeutic procedures to treat diseases of the bone. Preferably, the cells are useful in enhancing fusion of bone following a spinal fusion procedure. ADAS cells can be co-grafted with other cells, both genetically modified and non-genetically modified cells which exert beneficial effects on the mammal. Therefore the methods disclosed herein can be combined with other therapeutic procedures as would be understood by one skilled in the art once armed with the teachings provided herein.

The ADAS cells may be administered with other beneficial drugs or biological molecules (growth factors, trophic factors). When the ADAS cells are administered with other agents, they may be administered together in a single pharmaceutical composition, or in separate pharmaceutical compositions, simultaneously or sequentially with the other agents (either before or after administration of the other agents). Bioactive factors which may be co-administered include, but are not limited to, an anti-apoptotic agent (i.e., erythropoietin, thrombopoietin, insulin-like growth factor I and insulin-like growth factor II, hepatocyte growth factor, caspase inhibitors); an anti-inflammatory agent (i.e., p38 MAPK inhibitors, TGF-beta inhibitors, statins, IL-6 and IL-1 inhibitors, and non-steroidal anti-inflammatory drugs); an immunosupressive/immunomodulatory agent; an mTOR inhibitor; an anti-proliferative (i.e., azathioprine, mycophenolate mofetil); a corticosteroid (i.e., prednisolone, hydrocortisone); an anti-thrombogenic agent; and an anti-oxidant.

The invention encompasses administering ADAS cells to a mammal as undifferentiated cells, i.e., as cultured in growth medium. Alternatively, ADAS cells may be administered following exposure in culture to conditions that stimulate differentiation toward a desired phenotype, for example, an osteogenic phenotype.

The cells of the invention may be surgically implanted, injected, delivered (e.g., by way of a catheter or syringe), or otherwise administered directly or indirectly to the site in need of repair or augmentation. The cells may be administered by way of a matrix (e.g., a three-dimensional scaffold). The cells may be administered with conventional pharmaceutically acceptable carriers. Routes of administration of the cells of the invention or components (e.g., extracellular matrix, cell lysate, conditioned medium) thereof include intramuscular, ophthalmic, parenteral (including intravenous), intraarterial, subcutaneous, oral, and nasal administration. Particular routes of parenteral administration include, but are not limited to, intramuscular, subcutaneous, intraperitoneal, intracerebral, intraventricular, intracerebroventricular, intrathecal, intracisternal, intraspinal and/or peri-spinal routes of administration. Preferably, the cells are used in spinal fusion procedures.

The cells of the invention can be introduced alone or in admixture with a composition useful in the repair of bone wounds and defects. Such compositions include, but are not limited to bone morphogenetic proteins, hydroxyapatite/tricalcium phosphate particles (HA/TCP), gelatin, poly-L-lysine, and collagen. For example, the cells of the invention may be combined with demineralized bone matrix (DBM) or other matrices to make the composite osteogenic (bone forming in it own right) as well as osteoinductive.

To enhance the differentiation, survival or activity of implanted cells, additional bioactive factors as discussed elsewhere herein may be added. For example, a bioactive factor can include, but is not limited to bone morphogenetic protein, vascular endothelial growth factor, fibroblast growth factors, and other cytokines that have either osteoconductive and/or osteoinductive capacity. To enhance vascularization and survival of transplanted bone tissue, angiogenic factors such as VEGF, PDGF or bFGF can be added either alone or in combination with endothelial cells or their precursors.

Alternatively, ADAS cells to be transplanted may be genetically engineered to express such growth factors, antioxidants, antiapoptotic agents, anti-inflammatory agents, or angiogenic factors.

Pharmaceutical Compositions

Also encompassed within the scope of the invention are ADAS cell-products, including but not limited to extracellular matrices secreted by the ADAS cells themselves, cell lysates (e.g., soluble cell fractions) of ADAS cells, and ADAS cell-conditioned medium. As such, in terms of administering a composition comprising an ADAS cell, the invention includes a pharmaceutical composition comprising at least one of the following: an ADAS cell, an extracellular matrix produced thereby, a cellular lysate thereof, or an ADAS-conditioned medium. The pharmaceutical composition of the invention preferably includes a pharmaceutically acceptable carrier or excipient. The pharmaceutical composition is preferably used for treating bone conditions as defined herein.

Pharmaceutical compositions of the invention may comprise homogeneous or heterogeneous populations of ADAS cells, extracellular matrix or cell lysate thereof, or conditioned medium thereof in a pharmaceutically acceptable carrier. Pharmaceutically acceptable carriers for the cells of the invention include organic or inorganic carrier substances suitable which do not deleteriously react with the cells of the invention or compositions or components thereof. To the extent they are biocompatible, suitable pharmaceutically acceptable carriers include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art and are described, for example, in Pharmaceutical Sciences (17.sup.th Ed., Mack Pub. Co., Easton, Pa.) and WO 96/05309, each of which are incorporated by reference herein.

As another example but not by way of limitation, the cells of the invention may be administered alone, in a pharmaceutically acceptable carrier, or seeded on or in a matrix as described elsewhere herein, can be used to repair or replace damaged or destroyed bone tissue, to augment existing bone tissue, to introduce new or altered tissue, or to modify artificial prostheses.

When cells are administered in semi-solid or solid devices, surgical implantation into a precise location in the body is typically a suitable means of administration. In the case where the cells are administered in the form of a liquid or fluid pharmaceutical composition, the cells may be administered to a more general location (i.e. throughout a diffusely affected area), from which they migrate to a particular location (i.e. by responding to chemical signals).

Other embodiments encompass methods of treatment by administering pharmaceutical compositions comprising ADAS cellular components (e.g., cell lysates or components thereof) or products (e.g., extracellular matrix, trophic and other biological factors produced naturally by ADAS cells or through genetic modification, conditioned medium from ADAS culture). Again, these methods may further comprise administering other active agents as disclosed elsewhere herein.

The ADAS cells may also be applied with additives to enhance, control, or otherwise direct the intended therapeutic effect. Similarly, the cells may be applied with a biocompatible matrix which facilitates in vivo tissue engineering by supporting and/or directing the fate of the implanted cells.

Prior to the administration of the ADAS cells into a mammal, the cells may be stably or transiently transfected or transduced with a nucleic acid of interest using a plasmid, viral or alternative vector strategy. The cells may be administered following genetic manipulation such that they express gene products that intended to promote the therapeutic response(s) provided by the cells.

ADAS cells of the invention may be used to treat mammals requiring the repair or replacement of bone tissue resulting from disease or trauma or failure of the tissue to develop normally. Treatment may entail the use of the cells of the invention to produce new bone tissue. For example, the undifferentiated or osteogenic differentiation-induced cells of the invention may be used to treat bone conditions, including metabolic and non-metabolic bone diseases. Examples of a bone condition includes, but is not limited, a bone fracture, a bone/spinal deformation, osteosarcoma, myeloma, bone dysplasia, scoliosis, osteoporosis, osteomalacia, rickets, fibrous osteitis, renal bone dystrophy, and Paget's disease of bone.

Spinal Fusion

As set forth herein, back pain remains a major public health problem, especially among aged people. Persistent and severe back pain often causes debility and disability. This pain is closely associated with intervertebral disc abnormalities of the spine. Based on the present disclosure, degenerated discs may be treated by restoring the damaged tissues within the disc. The ADAS cells of the invention may be used to stimulate bone development and thereby restore the intervertebral discs at various stages of degeneration.

However, it is often necessary to remove at least a portion of the damaged and/or malfunctioning back component. For example, when a disc becomes ruptured, a discectomy surgical procedure can be performed to remove the ruptured disc and to fuse the two vertebrae between the removed disc together. Spinal fusion is a process by which two or more of the vertebrae that make up the spinal column are fused together with bone grafts and internal devices (such as rods) that heal into a single solid bone. Spinal fusion can eliminate unnatural motion between the vertebrae and, in turn, reduce pressure on nerve endings. In addition, spinal fusion can be used to treat, for example, injuries to spinal vertebrae caused by trauma; protrusion and degeneration of the cushioning disc between vertebrae (sometimes called slipped disc or herniated disc); abnormal curvatures (such as scoliosis or kyphosis); and weak or unstable spine caused by infections or tumors. The present invention encompasses compositions and methods for improving the success rates of spinal fusion procedures.

Since the ADAS cells of the present invention have been shown to form bone in vivo, the ADAS cells may be used in the place of bone grafts conventionally used in spinal fusion surgeries. Specifically, the ADAS cells may be used to stimulate bone formation between two adjacent vertebrae (within the vertebral body), as well as between adjacent transverse processes (within the intertransverse process spaces on either side of the spine).

ADAS cells of the present invention have numerous applications in the treatment of spine disorders, including promoting the production of proteoglycan rich matrix in intervertebral disc repair, producing bone for the intervertebral body in intertransverse process spinal fusion, and producing bone for long bone fracture healing. The present invention is based on the discovery that ADAS cells can be used to facilitate bone fusion in a spinal fusion procedure.

When a disc becomes ruptured, a discectomy surgical procedure can be performed to remove the ruptured disc and to fuse the two vertebrae between the removed disc together. Details regarding typical implementations of methods for fusing vertebrae are disclosed in U.S. Pat. Nos. 6,033,438 and 5,015,247, the contents of which are incorporated in their entireties herein by reference.

Disc degeneration is commonly treated with a segment fusion, whereby both the anterior and posterior spine elements of the interbody space are fused. It is important to consider the mechanical stresses place on the anterior and posterior elements when considering a fusion technique. The anterior motion segment elements (vertebral bodies and disc) bear approximately 80% of the compressive force at that given level in the spine. The posterior ⅓ of the vertebral body and disc represent the center point for axial compression in the spine. These mechanics are critical for assessing what type of fusion will have the best clinical outcome for a given pathology. The invention provides a spinal fusion procedure in which ADAS cells are used as a source of a bone substitute.

In one embodiment, the invention includes methods for performing one or more spinal fusions in a mammal comprising introducing an effective amount of ADAS cells into one or more suitable interbody spaces in the mammal by injection the cells through a syringe, catheter, or cannula to facilitate single, or multi level spinal fusion. The ADAS cells are to set under physiological conditions, i.e., in vivo, over time where the cells differentiate and form bone. The presence of the ADAS cells enhance the fusion of bone in a spinal fusion procedure.

In another embodiment, the invention includes methods for performing one or more spinal fusion on a mammal comprising placing in the posterior portion of at least one suitable interbody space a metallic implant selected from rods and pedicle screws or plates and pedicle screws by attachment thereof to adjacent vertebrae; injecting into the anterior portion of the interbody space an effective amount of ADAS cells; and allowing the ADAS cells to differentiate into a cell that exhibits at least one characteristic of a bone cell and thereby form bone in vivo.

The invention includes methods for performing spinal fusions by using either an anterior, posterior, or posterolateral approach to the interbody space. The posterolateral approach (unilateral or bilateral) reduces surgical morbidity over an anterior approach, but caution is required while working around the cauda equina and exiting nerve roots in the spinal canal. Posterior access and visualization of the interbody space is more limited than with the anterior approach, but many spinal surgeons are trained in how to deal with those circumstances.

As discussed elsewhere herein, the ADAS cells can also comprise an amount of one or more active bioactive agents suitable to promote bone growth, such as a growth factor, a bone morphology protein, or a pharmaceutical carrier therefor.

One mechanism by which the ADAS cells may provide a therapeutic or structural benefit is by incorporating themselves or their progeny into newly generated, existing or repaired tissues or tissue components. For example, ADAS cells and/or their progeny may incorporate into newly generated bone other structural or functional tissue and thereby cause or contribute to a therapeutic or structural improvement. Another mechanism by which the ADAS cells may provide a therapeutic or structural benefit is by expressing and/or secreting molecules, e.g., growth factors, that promote creation, retention, restoration, and/or regeneration of structure or function of a given tissue or tissue component.

The ADAS cells may also be used in combination with other cells or devices such as synthetic or biologic scaffolds, materials or devices that deliver factors, drugs, chemicals or other agents that modify or enhance the relevant characteristics of the cells as further described herein.

In accordance with the invention disclosed herein, the ADAS cells can be delivered to the mammal soon after harvesting the adipose tissue from the mammal. For example, the cells may be administered immediately after processing of the adipose tissue and obtaining a composition of ADAS cells. Ultimately, the timing of delivery will depend upon mammal availability and the processing time required to process the adipose tissue. In another embodiment, the timing for delivery may be relatively longer if the cells to be re-infused to the mammal are subject to additional modification, purification, stimulation, or other manipulation, as discussed herein. The number of cells administered to a mammal may be related to, for example, the cell yield after adipose tissue processing. A portion of the total number of cells may be retained for later use or cyropreserved.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations which are evident as a result of the teachings provided herein.

The following experiments were performed to determine the role of ADAS cells on the outcome of a spinal fusion procedure. For example the effect of syngeneic and allogeneic ADAS cells on spinal fusion procedures. The results herein demonstrate that ADAS cells are osteogenic and contribute to improvement in spinal fusion. Based on the present disclosure, ADAS cells can be used to treat mammals including, but are not limited to, trauma victims, osteoporotic mammals lacking suitable numbers of osteogenic cells, and mammals with non-union fractures.

Example 1

Alternatives to Autograft Bone in Spinal Fusion Surgery

Over 75% of the American population suffers from back pain. In some instances, underlying medical illnesses can contribute to back pain. These include scoliosis, spinal stenosis, degenerative disc disease, infectious processes, tumors, and trauma. For 1% of the population, the back pain is so severe that they are forced to go onto lifetime disability; an additional 1% of the population is incapacitated by back pain for a limited time period. The majority of the mammals with back pain are treated with conservative therapies; however, when modalities such as bed rest and medication fail, physicians often recommend spinal fusion surgery. The goal of this operation is to form ectopic bone between two or more adjacent vertebra, "fusing" them together into a solid structure. Immobilization of the vertebral joint reduces the pressure on nerve roots leaving the spinal cord and the resulting painful sensation. Surgeons use a poster lateral approach to the lumbar spine, introducing a bone graft or osteoinductive material with a mechanical support between two vertebral bodies to form ectopic bone (FIG. 1).

Without wishing to be bound by any particular theory, it is believed that the "ideal" graft material for a spinal fusion would provide the following properties: mechanical support (material stabilizes the spine/surgical site during the recovery period); osteoconductive (material facilitates the ingrowth and integration of adjacent bone upon itself); osteoinductive (material recruits and stimulates the formation and growth of bone from cells that may not naturally do so); and osteogenic (material contains cells that themselves are capable of forming new bone).

At present, the "gold standard" for spinal fusion repair is autologous bone, usually harvested from the iliac crest of the individual. Surgeons transplant the mammal's own bone to the site of need. Nevertheless, this is far from a perfect solution. In 30% of mammals, the donor site becomes infected, bruised, fractured, or painful following the surgery. Indeed, when a mammal requires autograft bone for multiple spinal fusions, the iliac crest may not provide sufficient material. The underlying health of the mammal further influences the outcome of spinal fusion surgery. Mammals with osteoporosis or vascular insufficiency due to diabetes, smoking, or age display reduced new bone formation and non-union at the site of the spinal fusion (Whang et al., 2003, Spine J. 3:155-65). Thus, there is a need for alternatives to autograft bone in spinal fusion surgery.

While there are alternative materials available, all face a common limitation; none display osteogenic capability. Allograft bone from cadavers can be sterilized, stored, and used in the operating room as needed. These materials can be pre-shaped for specific use or powdered, allowing them to be applied as a paste at the surgical site; however, allografts can cause inflammation, elicit an immune response, and have been an infectious source in a limited number of cases (Whang et al., 2003, Spine J. 3:155-65). Because allograft bone is sterilized, it no longer contains viable native bone forming cells (osteoblasts, osteocytes) and lacks osteogenic properties. In clinical trials, allograft bone is inferior to autograft bone in multilevel spinal fusions (Whang et al., 2003, Spine J. 3:155-65). Ceramic materials, such as hydroxyapatite and tricalcium phosphate (HA/TCP), are osteoconductive and promote new bone formation. However, they lack osteogenic and osteoinductive properties, limiting their utility. While osteoinductive growth factors such as bone morphogenetic proteins (BMP) are available commercially (Infuse™ from Sofamor/Medtronics), they require the presence of osteogenic cells within the spinal fusion site to promote new bone formation (Whang et al., 2003, Spine J. 3:155-65). The development of an osteogenic cell has the potential to improve the outcome with any of these alternative spinal fusion materials.

A number of animal species have served as models in pre-clinical spinal fusion trials. These include the rat, rabbit, dog, sheep, goat, and non-human primate (Khan et al., 2004, Biomaterials 25:1475-85; Liebschner et al., 2004, Biomaterials 25:1697-714; Sandhu et al., 2001, Eur. Spine J. 10:S122-31). Of these, the rat (Boden et al., 1998, Spine 23:2486-92; Cui et al., 2001, Spine 26:2305-10; Wang et al., 2003, J. Bone Joint Surg. Am. 85-A:905-11) and rabbit (Khan et al., 2004, Biomaterials 25:1475-85; Kruyt et al., 2004, Biomaterials 25:1463-73) have been used for "proof of concept" studies due to the animal's size and cost. In each species, surgeons can use a postero lateral approach to the lumbar spine, similar to that used to treat other mammals. The rabbit is more commonly used for spinal fusion feasibility studies (Khan et al., 2004, Biomaterials 25:1475-85), in part due to the animal's size and the confirmed observation that the rate of spinal fusion in the rabbit is similar to that observed in a human. Nevertheless, the rabbit presents certain disadvantages compared to the rat model. Unlike rats, where well-characterized inbred strains are available, laboratory rabbits do not display syngeneic or congenic haplotypes. Thus, it may not be possible to routinely transplant cells from one rabbit to the other without the risk of rejection. The rat poster lateral spinal fusion model has been employed successfully to demonstrate the osteoinductive effect of bone morphogenetic protein 7 when presented in a collagen scaffold (Salamon et al., 2003, J. Spinal Disord. Tech. 16:90-5). Several groups have used the rat model successfully to evaluate the osteogenic effect of bone marrow stromal cells on spinal fusion (Boden et al., 1998, Spine 23:2486-92; Cui et al., 2001, Spine 26:2305-10; Wang et al., 2003, J. Bone Joint Surg. Am. 85-A:905-11). They achieved statistically significant improvements in spinal fusion within 4 to 9 weeks following implantation of bone marrow stromal cells compared to scaffold alone. Each study used cohorts of n=4 to 8 animals.

The following experiments are designed to assess the role of ADAS cells in spinal fusion procedures.

Isolation of ADAS Cells

Subcutaneous adipose tissue is harvested from male Fischer rats (8 to 10 weeks of age, n=25, yielding approximately 3 grams tissue per rat). ADAS cells are prepared according to published methodologies (Aust et al., 2004, Cytotherapy 6:7-14; Halvorsen et al., 2001, Metabolism 50:407-413; Sen et al., 2001, Journal of Cellular Biochemistry 81:312-319). Breifly, adipose tissue is minced, washed, and suspended in an equal volume of phosphate buffered saline containing 1% bovine serum albumin and 0.1% collagenase type I (Worthington Biochemical, Lakewood N.J.). Following a 60-minute digestion at 37° C. with agitation (50 rpm), the suspension is centrifuged at 1200 rpm for 5 minutes at room temperature and the stromal vascular fraction cells pelleted. The stromal vascular cells are plated at a density of 0.1 grams of tissue digest per $cm^2$ in "Stromal Media" (DMEM/F-12 Ham's Media supplemented with 10% fetal bovine serum (Hyclone, Logan Utah) and 1% antibiotic/antimycotic. The cells are incubated for 3 to 6 days in a humidified 5% $CO_2$ incubator until they reach 75% confluency. This yields approximately $25-30 \times 10^4$ cells/$cm^2$. At that time, ADAS cells are harvested by digestion with trypsin/EDTA and passaged at a plating density of $5 \times 10^3$ cells/$cm^2$. Cells are expanded for up to 2 passages to obtain >60 million cells (Table 1). Cells are evaluated in vitro for their osteogenic and adipogenic capacity using standard assays over a 1 to 3 week inductive period as described in (Halvorsen et al., 2001, Tissue Eng. 7:729-41; Hicok et al., 2004, Tissue Engineering 10:371-380). Cells can be cryopreserved in liquid nitrogen prior to use.

To track the cells histologically, the cells are labeled during the initial passage with a retroviral vector carrying the LacZ gene expressing β-galactosidase to provide a trackable marker. Stable integration of retroviral vectors reduces the risk that the marker will be lost during the time of implantation. This method has been used routinely to track implanted cells.

TABLE 1

Estimated ADAS Cell Yield and Expansion

| Passage | Initial Passage | Second Passage |
| --- | --- | --- |
| ADAS Cells/gm | $2.5 \times 10^5$ | $1.25 \times 10^6$ |
| ADAS Cells/Adipose tissue from 25 rats (~75 gm) | $18.75 \times 10^6$ | $93.75 \times 10^6$ |

Example 2

ADAS Cell Osteogenesis In Vitro

Figure 3:
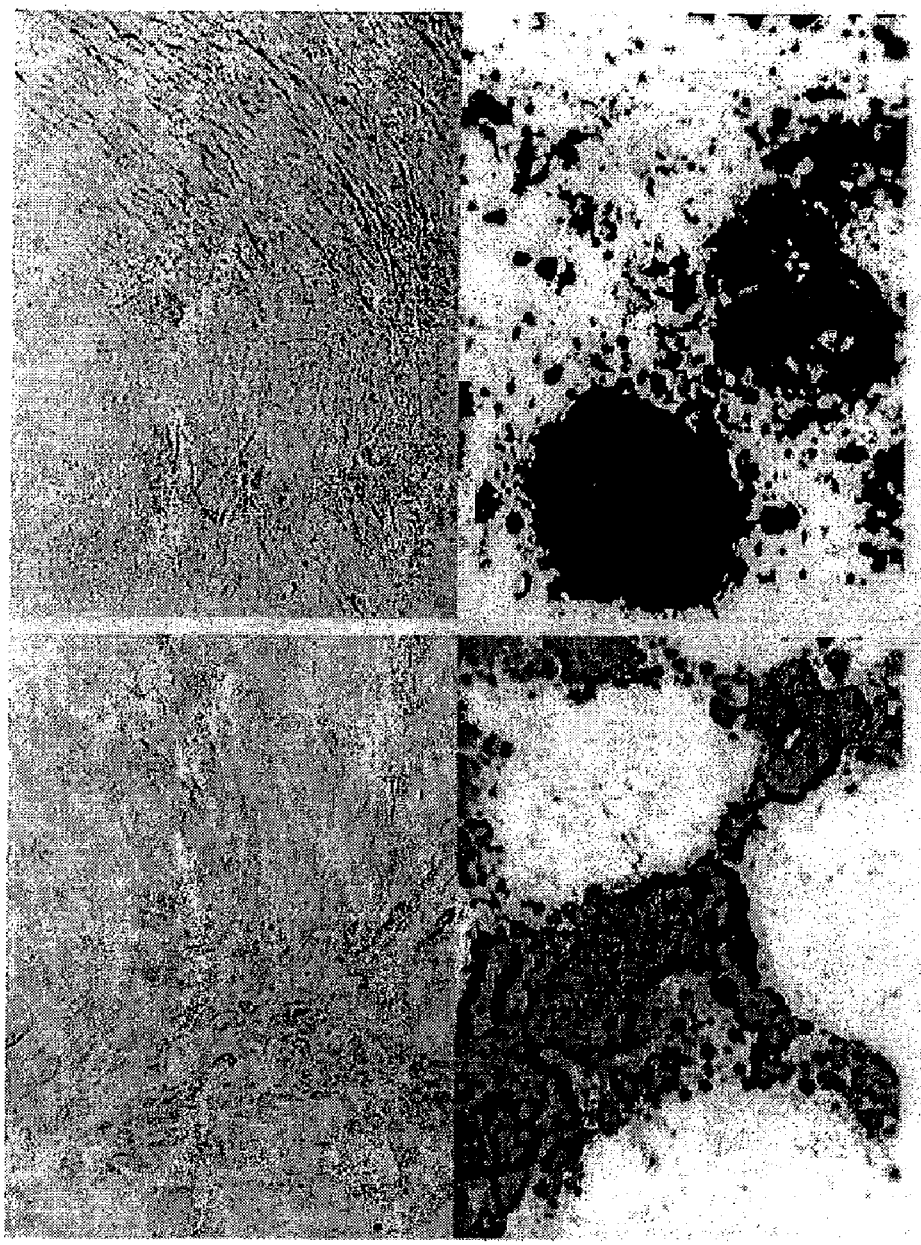
FIG. 3 is an image depicting osteogenesis of human ADAS cells.

It has been demonstrated that human ADAS cells display an osteogenic phenotype in vitro when cultured in the presence of ascorbate, β-glycerophosphate, dexamethasone, and 1,25 dihydroxyvitamin $D_3$ (Halvorsen et al., 2001, Tissue Eng. 7:729-41). Under these conditions, the ADAS cells mineralize their extracellular matrix as demonstrated by positive staining with either Alizarin Red or von Kossa for calcium phosphate deposition (FIG. 3).

Figure 4:
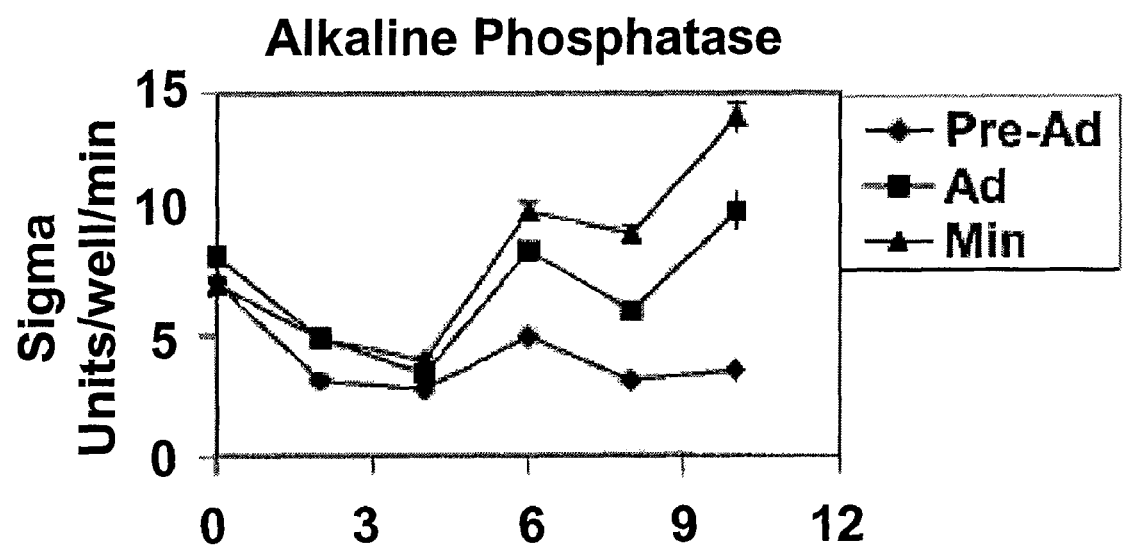
FIG. 4 is a chart depicting the aldehyde phosphatase expression in ADAS cells during adipogenic and osteogenic differentiation.

It was observed that human ADAS cell osteogenesis over a 10-day period was accompanied by an increase in alkaline phosphatase activity. At the end of the culture period, osteogenic cells (mineralized) displayed a 3-fold higher level of alkaline phosphatase relative to cells maintained under control conditions (FIG. 4). Likewise, there was a time dependent increase in secreted levels of osteocalcin protein under osteogenic conditions. The ADAS cells expressed a number of gene markers consistent with an osteoblast phenotype, including osteocalcin, osteopontin, bone morphogenetic proteins (BMP) 2 and 4, and the BMP receptors IA, IB, and II.

Figure 2:
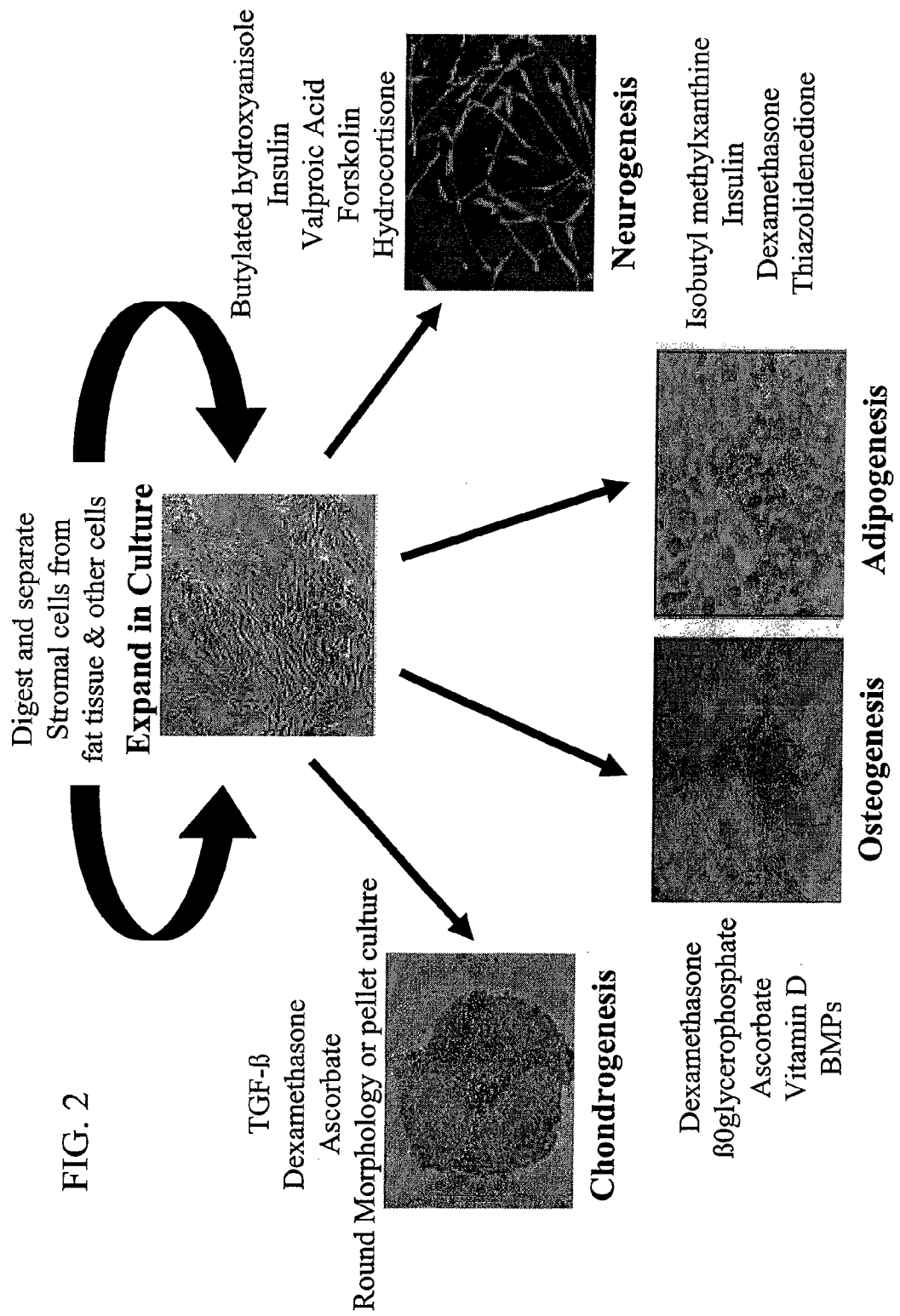
FIG. 2 is an image depicting the potential of ADAS cells to differentiate along multiple lineage pathways. In response to specific cocktails of chemicals and growth factors, human ADAS cells can differentiate into chondrocytes, osteoblasts, adipocytes, and neuronal- and glial-like cells in vitro.

It has also been demonstrated that ADAS cells have the potential to differentiate along multiple lineage pathways. In response to specific cocktails of chemicals and growth factors, ADAS cells can differentiate into chondrocytes, osteoblasts, adipocytes, and neuronal- and glial-like cells in vitro (FIG. 2).

Example 3

ADAS Cells are Osteogenic In Vivo

Figure 5B:
FIG. 5 is an image demonstrating that ADAS cells form bone in vivo.
Figure 5A:

To extend the in vitro findings, human ADAS cells were transplanted into immunodeficient SCID mice. The ADAS cells were loaded onto three $cm^3$ cubes of hydroxyapatite/tricalcium phosphate (HA/TCP) scaffold and implanted subcutaneously. After a 6-week period, the implants were harvested, fixed, decalcified, and stained with Hematoxylin/Eosin or with human nuclear antigen specific antibodies (FIG. 5). Based on H&E staining, it was observed that new bone formed adjacent to the hydroxyapatite/tricalcium phosphate scaffold in the presence of the human ADAS cells. The human cells were identified within the bone based on immunofluorescent analysis with the human antigen specific antibody. In the presence of the scaffold alone (no cells), new bone did not form and no human cells were detected. These studies demonstrate that ADAS cells are capable of osteogenesis in vivo.

Example 4

ADAS Cells can be Transplanted Allogeneically

The following experiments serve to provide proof of concept regarding the allogeneic transplantation of ADAS cells in the spinal fusion model. It has been demonstrated that ADAS cells fail to elicit a proliferative response from allogeneic lymphocytes in a mixed lymphocyte reaction. Without wishing to be bound by any particular theory, it is believed that ADAS cells release a factor that inhibits the lymphocyte's immune response to allogeneic antigens. The presence of ADAS cells prolonged skin graft survival in the baboon model, and therefore indicates that adult stem cells can be transplanted allogeneically for tissue engineering applications.

Using a canine model, a critical sized segmental defect in the femoral diaphysis of dogs can be created. The defects can be repaired with hydroxyapatite/tricalcium phosphate scaffolds alone or in combination with either autologous or allogeneic ADAS cells; the allogeneic cells are mismatched for both the HLA-1 and HLA-2 antigens (Table 2). The transplant recipients do not receive any immunosuppressive therapy. The animals are sacrificed 16 week later, and the degree of bone repair observed in the presence of ADAS cells can be compared with transplant of scaffold alone (no ADAS cells). Without wishing to be bound by any particular theory, it is believed that there will be no observable significant difference between the repair obtained with autologous versus allogeneic ADAS cells, nor will there be evidence of any immune response to the allogeneic cells. These experiments serve to demonstrate the fact that allogeneic transplantation of adult stem cells in a tissue engineered construct is feasible, and in some instances does not require immunosuppressive therapy.

TABLE 2

Histomorphometric Analysis of Bone and Ceramic in Canine Segmental Defects**

| Implant Type | Percent Ceramic | Percent Bone |
| --- | --- | --- |
| Allogeneic MSC-ceramic implants (n = 4) | 35 ± 3% | 49 ± 12%[#] |
| Autologous MSC-ceramic implants (n = 6) | 33 ± 5% | 42 ± 5%[#] |
| Cell free ceramic implants | 30 ± 6% | 25 ± 12% |

**Percent Ceramic was the percentage of the implant total area occupied by the ceramic, and the Percent Bone was the percentage of the porous space occupied by bone. Values are given as the mean ± standard deviation.
[#]Compared to the cell free implants, the difference was significant ($p < 0.05$) (Arinzeh et al., 2003, J. Bone Joint Surg. Am. 85-A: 1927-35).

Example 5

Syngeneic ADAS Cells on Spinal Fusion

The following experiments serve to address the hypothesis that ADAS cells are osteogenic in vivo and, in combination with a suitable biomaterial carrier, can improve and accelerate spinal fusion in animal models. Table 3 summarizes the experimental design. The initial studies are conducted with syngeneic ADAS cells (cells from the same strain of rat), to mimic the conditions existing in a human autologous cell transplant. By removing issues relating to immune response and rejection, these experiments focus on the osteogenic capacity of ADAS cells for spinal fusion. These experiments using rat as a spinal fusion model are patterned to methods known in the art (Boden et al., 1995, Spine 20:412-20; Wang et al., 2003, J. Bone Joint Surg. Am. 85-A:905-11; Cui et al., 2001, Spine 26:2305-10; Sandhu et al., 2001, Eur. Spine J. 10 Suppl. 2:S122-31; Wang et al., 2003, Spine J. 3:155-65).

Surgical Procedure and Euthanasia

A single level intertransverse spinal arthrodesis (L4-L5) on 96 female Fischer rats are performed as described by Cui (Cui et al., 2001, Spine 26:2305-10). Animals are anesthetized with ketamine (80 mg/kg) and xylazine (7 mg/kg), shaved, draped, and their skin disinfected with Betadine and 70% ethanol. A midline posterior longitudinal incision is made from L3 to L5. The periosteum is raised along the spinous processes and lamina to the lateral aspect of the facets. The facets are removed using a rongeur and the wound is irrigated with saline solution. Animals are randomized into cohorts of n=32. Cohort A receives no treatment. Cohort B receives the implantation of hydroxyapatite/tricalcium phosphate (40 mg) alone into the fusion bed. Cohort C receives implantation of hydroxyapatite/tricalcium phosphate (40 mg) in combination with $2 \times 10^6$ ADAS cells derived from the subcutaneous adipose tissue of Fischer rats (syngeneic cells) into the fusion bed. Following the placement of the implant, the deep fascia and skin incisions are closed. Animals receiving buprenorphine hydrochloride (0.1 mg/kg) for post-operative analgesia are monitored for recovery of mobility and function for up to 24 hours following the procedure. Groups of 16 animals from each Cohort are sacrificed by $CO_2$ asphyxiation 6 and 12 weeks after the surgical procedure. At that time, serum specimens and the lumbar spine are collected for analysis.

Radiographic Follow-Up

Animals are subjected to posteroanterior and lateral radiographs of the lumbosacral spine following surgery and at 6 week intervals following surgery. The radiographic analysis serve to detect ectopic bone formation and callus formation in the lumbar spine at the surgical site. Micro computerized tomography (micro-CT) are performed on the dissected specimens following sacrifice. The structure and volume of new bone formation can be determined using methods known in the art (Mankani et al., 2004, Radiology 230:369-76).

Manual Palpation of Spinal Fusion

At the time of sacrificing the animals, the L3-L5 lumbar spine are dissected from the animals. The specimens are palpated for extension and flexion at L3-4 and L4-5. The specimens are graded for the presence or absence of any motion. Those specimens with motion in any direction receive a score of "0" while those without motion in any dimension are considered "fused" with a score of "1" (Cui et al., 2001, Spine 26:2305-10; Grauer et al., 2004, Spine J. 4:281-6).

Biomechanical Testing of Spinal Fusion

Before testing, all muscle are cleared and the intervertebral disc at L4-5 are divided so that only the fusion mass is connecting the two vertebrae. Steel k-wire (3.2 mm) pins are placed in an antero-posterior direction into the vertebral bodies. Uniaxial tensile testing are performed at a displacement rate of 0.5 cm/minute with the load applied through the k-wire. Displacements are measured by extensometers and the loads measured by a load cell. The peak load to failure is measured from computer generated load displacement plot. Stiffness is determined as the slope of the line between two points (at 50% and 75% load to failure) on the load displacement curve. The adjacent segment at L3-4 is tested in a similar manner.

Histological Analysis

The lumbar spine specimens (n=8 at each time point for each Cohort) is fixed in formalin for 48 hours, decalcified in 0.25 M ethylenediaminetetraacetic acid in phosphate buffered saline for 2 weeks at 4° C., and incubated for 16 hours in a solution of X-gal (1 mg/ml) at 37° C. The specimen is paraffin embedded, sectioned transversely (5 μm), and stained with hematoxylin and eosin. Ten sections from each specimen are analyzed using the Medivue (Nikon) software to quantify the mean percentage (±standard deviation) of each implant occupied by ectopic bone.

Without wishing to be bound by any particular theory, it is believed that ADAS cells are successful for spinal fusion if the following outcomes are achieved: 1) minimal evidence of fusion (manual manipulation fusion score of 0 in 90% of animals, no radiographic evidence of ectopic bone, and less than 5% of the area of the surgical site occupied by bone matrix in 10 sections per specimen based on histology and CT analysis) in Cohort A (no treatment) at the 6 and 12 week time points is observed; 2) detection of the HA/TCP scaffold in histological analysis of animals in Cohorts B and C at the 6 and 12 week time points; 3) minimal evidence of fusion (manual manipulation fusion score of 0 in 90% of animals, no radiographic evidence of ectopic bone, and less than 5% of the area of the surgical site occupied by bone matrix in 10 sections per specimen based on histology and CT analysis) in Cohort B (HA/TCP alone) at the 6 and 12 week time points; 4) detection of transplanted ADAS cells in Cohorts C for 6 weeks following surgery based on β-galactosidase enzyme activity or immunodetection on histological analysis; and 5) superior spinal fusion in the presence of ADAS cells (Cohorts C) (manual manipulation fusion score of "1" in 90% of animals, radiographic evidence of ectopic bone at the surgical site, and greater than 30% of the area of the HA/TCP implant occupied by bone matrix in 10 sections per specimen based on histology and by CT analysis) relative to scaffold alone (Cohort B) or empty lesion (Cohort A) controls at the 6 and 12 week time points.

The experiments set forth in this Example serve to address the utility of ADAS cells to accelerate and improve lumbar spinal fusion in a rat model.

TABLE 3

Outline of Experimental Design

| Cohort | A<br>No Rx | B<br>Scaffold Only | C<br>Scaffold + Syngeneic Cells |
|---|---|---|---|
| Intertransverse Spinal L4-L5 Arthrodesis | | N = 96 Fischer rats | |
| Implants | N = 32 | N = 32 | N = 32 |
| HA-TCP scaffold | − | + | + |
| Fischer ADAS cells ($2 \times 10^6$) | − | − | + |
| Euthanize at 6 weeks | N = 16 | N = 16 | N = 16 |
| Euthanize at 12 weeks | N = 16 | N = 16 | N = 16 |
| In vivo analyses | Micro CT analysis, X-ray analysis, manual determination of spinal fusion (blinded analysis, 2 independent observers) | | |
| In vitro analyses | Histology (H&E) on decalcified tissue, biomechanical testing. | | |

Example 6

Allogeneic ADAS Cells on Spinal Fusion

The following experiments serve to address the hypothesis that ADAS cells can be transplanted allogeneically with a biomaterial scaffold to achieve a superior spinal fusion as compared to a biomaterial scaffold alone. Table 4 summarizes the experimental design. It has been shown that it is possible to transplant bone marrow derived MSCs to repair bone defects without evidence of significant immune rejection (Arinzeh et al., 2003, J. Bone Joint Surg. Am. 85-A:1927-35). The experiments disclosed herein demonstrate the utility of allogeneic ADAS cells in a lumbar spinal fusion model.

Fischer and ACI inbred rat strains are selected for the following experiments based on previous studies in the literature (Akahane et al., 1999, J. Bone Miner Res. 14:561-8; Yoshikawa et al., 2000, J. Bone Miner Res. 15:1147-57). These animals display a histocompatibility antigen mismatch and reject osteogenic tissue transplants unless given immunosuppressive therapy (Akahane et al., 1999, J. Bone Miner Res. 14:561-8; Yoshikawa et al., 2000, J. Bone Miner Res. 15:1147-57).

Isolated allogeneic ADAS cells from ACI rats are used for implantation into Fischer rat lumbar spinal fusion. The experiments herein can be conducted in parallel with the experiments relating to syngeneic autologous ADAS cells, thereby allowing for comparative analysis. The absence or presence of an immune response to the allogeneic ADAS cells can be assessed based on one-way mixed lymphocyte reactions and flow cytometric analysis of serum samples obtained from the Cohorts.

TABLE 4

Outline of Experimental Design

| Cohort | A<br>No Rx | B<br>Scaffold Only | D<br>Scaffold + Allogeneic Cells |
|---|---|---|---|
| Intertransverse Spinal L4-L5 Arthrodesis | | N = 96 Fischer rats | |
| Implants | N = 32 | N = 32 | N = 32 |
| HA/TCP | – | + | + |
| ACI ADAS cells ($2 \times 10^6$) | – | – | – |
| Euthanize at 6 weeks | N = 16 | N = 16 | N = 16 |
| Euthanize at 12 weeks | N = 16 | N = 16 | N = 16 |
| In vivo analyses | Micro CT analysis, X-ray analysis, manual determination of spinal fusion (blinded analysis, 2 independent observers) | | |
| In vitro analyses | Histology (H&E) on decalcified tissue, biomechanical testing, one-way mixed lymphocyte reaction, flow cytometric analysis of serum samples (to include Cohort C). | | |

Subcutaneous adipose tissue are harvested from male ACI rats (8 to 10 weeks of age, n=25, yielding approximately 3 grams tissue per rat) as discussed elsewhere herein. The number of cells obtained with each passage follows the estimates outlined in Table 1. The ADAS cells from the ACI rats are subjected to the same in vitro analyses as those employed for the Fischer rat ADAS cells. The surgical and follow up procedures (i.e. radiographic follow-up, manual palpation of spinal fusion) are performed as described elsewhere herein. The HA/TCP implants can contain about $2 \times 10^6$ cells in a 100 µl volume.

For histological analysis, the lumbar spine specimens are fixed in formalin for 48 hours, decalcified in 0.25 M ethylenediaminetetraacetic acid in phosphate buffered saline for 2 weeks at 4° C., and incubated for 16 hours in a solution of X-gal (1 mg/ml) at 37° C. The specimen are paraffin embedded, sectioned transversely (5 µm), and stained with hematoxylin and eosin. Ten sections from each specimen are analyzed using the Medivue (Nikon) software to quantify the mean percentage (±standard deviation) of each implant occupied by ectopic bone. Sections are evaluated for the presence or absence of infiltrating lymphocytes. Without wishing to be bound by any particular theory, an antibody against the pan-hematopoietic antibody (anti-CD45) can be used to immunohistochemical staining the cells to identify any immune cells within or around the implants. The number of infiltrating lymphocytes can be determined in 10 sections per specimen and quantified using the Medivue software program.

Serum Immune Response

Serum antibody binding to the ACI strain ADAS cells is evaluated by flow cytometry. ADAS cells from ACI rats are quickly thawed from liquid nitrogen storage and placed in culture for 5 days to facilitate maximum viability and surface antigen expression. The cells are harvested by trypsinization, washed in staining buffer (1× DPBS, 5% FBS, 0.5% BSA, 0.1% Sodium Azide), and resuspended at $5 \times 10^6$ cells/ml. 90 µl of cells ($5 \times 10^5$ cells) are aliquotted into 2 ml Eppendorf tubes. 10 µl of undiluted rat serum, or serum diluted 1:10 in staining buffer, is added to each tube to give effective dilutions of serum that are 1:10 and 1:100. All tubes are incubated on ice for 30 minutes, washed with wash buffer (1× DPBS, 0.5% BSA and 0.1% sodium azide), and then resuspended in 100 µl of staining buffer. Goat anti-rat (IgG/IgM) FITC secondary antibody is added to all tubes at a final dilution of 1:100. Control tubes receive ACI ADAS cells with secondary antibody only (negative control), or with a positive control Fischer anti-ACI rat serum that is produce by repeated immunization of Fischer rats with ACI ADAS cells. The suspensions are incubated in the dark on ice for 15 minutes and washed twice with wash buffer as discussed elsewhere herein. The cells are then fixed in 200 µl of 1% paraformaldehyde and allowed to incubate on ice, in fixative for at least 15 minutes prior to acquisition. 20,000 events are acquired for flow cytometry analysis. Results are expressed as the percentage of ACI cells stained with the secondary antibody based on increased mean fluorescent intensity relative to the secondary antibody alone negative control.

One-Way Mixed Lymphocyte Reaction (MLR)

This assay is based on the following rationale: if T cells are primed in vivo to ACI alloantigens, they will respond to restimulation in vitro at a faster kinetic rate. Recipient rat T cell activation to allogeneic ACI strain ADAS cells can be evaluated by the MLR assay. MLR assays are performed on individual rats using pooled mesenteric plus cervical LN cells as responder cells. Eight animals per group from 3 groups: No Treatment (Cohort A); scaffold only (Cohort B); scaffold +allogeneic cells (Cohort D) are assessed (Table 5). The assay is set up by culturing the responder cells in medium, with irradiated (5000R) syngeneic Fischer spleen stimulator cells, or with irradiated allogeneic ACI spleen stimulator cells. The T cell proliferation in response to medium or to syngeneic spleen cells represents background responses; the syngeneic response is typically subtracted from the response to allogeneic cells to assess true proliferation. As positive and negative controls, assays are set up with irradiated allogeneic ACI (positive) and syngeneic Fischer (negative) lymphocytes; their expression of both allogeneic versus syngeneic HLA 1 and 2 antigens insure either a robust proliferative response by the responder, Fischer derived lymphocytes, or no response. The MLR assay are performed in 96 well plates using triplicate wells per treatment. Responder cells are plated at $4 \times 10^5$ cells/well and spleen cell stimulators are plated at $1 \times 10^5$ cells/well. The culture medium used is Iscove's Modified Dulbecco's Medium plus 10% FBS (Hyclone) supplemented with non-essential amino acids, sodium pyruvate, 2-mercaptoethanol, and antibiotics/antimycotics. Replicate culture plates are prepared for harvesting on days 3 and 7 of culture. Cultures are pulsed on days 2 or 6 with $^3$H-thymidine (1 µCi/well) and the cells are harvested approximately 16 hours later for scintillation counting. Results are reported as counts per minute (cpm) which reflect the degree of T cell proliferation in the culture wells.

TABLE 5

One-Way Mixed Lymphocyte Reaction

| Responder Cells | | Stimulator Cells | |
|---|---|---|---|
| Cohort A - Lymph Node Cell | Medium Alone | Syngeneic Fischer Splenic Cells | Allogeneic ACI Splenic Cells |
| Cohort B - Lymph Node Cell | | | |
| Cohort C - Lymph Node Cell | | | |

Without wishing to be bound by any particular theory, it is believed that allogeneic ADAS cells are successful for spinal fusion if the following outcomes are achieved: minimal evidence of fusion (manual manipulation fusion score of 0 in 90% of animals, no radiographic evidence of ectopic bone, and less than 5% of the area of the surgical site occupied by bone matrix in 10 sections per specimen based on histology and CT analysis) in Cohort A (no treatment) at the 6 and 12 week time points; detection of HA/TCP scaffold in histologic analysis of all animals in Cohorts B and D at 6 and 12 week time points; minimal evidence of fusion (manual manipulation fusion score of 0 in 90% of animals, no radiographic evidence of ectopic bone, and less than 5% of the area of the surgical site occupied by bone matrix in 10 sections per specimen based on histology and radiographic analysis) in Cohort B (HA/TCP alone) at the 6 and 12 week time points; minimal evidence of fusion (manual manipulation fusion score of 0 in 90% of animals, no radiographic evidence of ectopic bone, and less than 5% of the area of the surgical site occupied by bone matrix in 10 sections per specimen based on histology and CT analysis) in Cohort B (HA/TCP alone) at the 6 and 12 week time points; detection of transplanted ADAS cells in Cohorts D for up to 6 weeks following surgery based on β-galactosidase enzyme activity on histologic analysis; superior spinal fusion in the presence of ADAS cells (Cohorts D) (manual manipulation fusion score of "1" in 90% of animals, radiographic evidence of ectopic bone at the surgical site, and greater than 30% of the area of the HA/TCP implant occupied by bone matrix in 10 sections per specimen based on histology and by CT analysis) relative to scaffold alone (Cohort B) or empty lesion (Cohort A) controls at the 6 and 12 week time points; less than a 1.5-fold increase in the level of anti-ADAS antibodies in Cohorts C and D (ADAS cell implants) relative to Cohorts A and B (no cell treatment); and no evidence of enhanced responder cell proliferation stimulated by allogeneic derived spleen cells as compared to medium alone or syngeneic derived spleen cells in the one-way mixed lymphocyte reaction when comparing Cohorts A, B and D. The mixed lymphocyte reaction positive controls will display at proliferative response of at least 10,000 cpm.

Example 7

Compare and Contrast the Relative Effectiveness of Syngeneic and Allogeneic ADAS Cells in a Spinal Fusion Model The disclosure presented herein provides data allowing for the determination of whether allogeneic (HLA mismatched) and syngeneic (HLA compatible) ADAS cells display equal function in achieving a spinal fusion. The experimental design is summarized in Table 6. Without wishing to be bound by any particular theory, it is believed that the two cell populations are equivalent, based on the previous studies that achieved a successful repair of a critical sized bone defect in dogs using allogeneic MSCs (Arinzeh et al., 2003, J. Bone Joint Surg. Am. 85-A:1927-35). The comparison of syngeneic and allogeneic ADAS cells provides significant medical and commercial implications. The disclosure presented herein provides for the use of allogeneic ADAS cells for tissue regeneration therapy.

TABLE 6

Comparison of Spinal Fusion with Allogeneic vs. Syngeneic ADAS Cells

| Parameter at 6 & 12 wks | Syngeneic (Cohort C) | Allogeneic (Cohort D) |
|---|---|---|
| Percentage of implant composed of bone based on histological analysis | N = 8 per time point | N = 8 per time point |
| Manual manipulation fusion scores | N = 16 per time point | N = 16 per time point |
| Radiographic measures of fusion | N = 16 per time point | N = 16 per time point |
| Biomechanical testing of fusion | N = 8 per time point | N = 8 per time point |

Without wishing to be bound by any particular theory, it is believed that allogeneic ADAS cells are comparable to syngeneic ADAS cells for success in spinal fusion if all the parameters in Table 6 do not show a statistically significant difference between the allogeneic and syngeneic ADAS cell Cohorts ($p>0.05$, preferably $p>0.30$).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of enhancing the fusion of bone following a spinal fusion procedure in a mammal, the method comprising administering an isolated adipose tissue derived adult stromal (ADAS) cell and a cellular lysate thereof to the spine of said mammal, wherein said ADAS cell differentiates in vivo into a cell that expresses at least one characteristic of a bone cell.

2. The method of claim 1, wherein said ADAS cell is cultured in vitro for a period of time without being induced to differentiate prior to the administration of said cell to the mammal.

3. The method of claim 1, wherein said ADAS cell is allogeneic with respect to said mammal.

4. The method of claim 1, wherein said ADAS cell induces bone formation for intervertebral body spinal fusion.

5. The method of claim 1, wherein said ADAS cell induces bone formation for intertransverse process spinal fusion.

6. The method of claim 1, wherein the ADAS cell is administered with a biocompatible matrix.

7. The method of claim 1, wherein said biocompatible matrix is selected from the group consisting of calcium alginate, agarose, fibrin, collagen, laminin, fibronectin, glycosaminoglycan, hyaluronic acid, heparin sulfate, chondroitin sulfate A, dermatan sulfate, and bone matrix gelatin.

8. The method of claim 1, wherein said ADAS cell is genetically modified.

9. The method of claim 1, wherein said ADAS cell is administered into one or more interbody spaces in the spine of the mammal.

10. The method of claim 1, wherein the spinal fusion is in a segment of the spine selected from the group consisting of cervical, thoracic, lumbar, lumbosacral and sacro-iliac (SI) joint.

11. The method of claim 1, wherein said ADAS cell is administered into one or more interbody spaces by an approach selected from the group consisting of a posterior approach, a posterolateral approach, an anterior approach, an anterolateral approach, and a lateral approach.

12. The method of claim 1, wherein said mammal is a human.

13. A method of performing one or more spinal fusions in a mammal, the method comprising administering an isolated adipose tissue-derived adult stromal (ADAS) cell and a cellular lysate thereof to the spine of said mammal to facilitate a single or multi-level spinal fusion.

14. The method of claim 13, wherein said ADAS cell differentiates in vivo into a cell that expresses at least one characteristic of a bone cell.

15. The method of claim 13, wherein said ADAS cell is cultured in vitro for a period of time without being induced to differentiate prior to the administration of said cell to said mammal.

16. The method of claim 13, wherein said ADAS cell is allogeneic with respect to the mammal.

17. The method of claim 13, wherein the ADAS cell induces bone formation for intervertebral body spinal fusion.

18. The method of claim 13, wherein the ADAS cell induces bone formation for intertransverse process spinal fusion.

19. The method of claim 1, wherein the ADAS cell is administered with a biocompatible matrix.

20. The method of claim 13, wherein said biocompatible matrix is selected from the group consisting of calcium alginate, agarose, fibrin, collagen, laminin, fibronectin, glycosaminoglycan, hyaluronic acid, heparin sulfate, chondroitin sulfate A, dermatan sulfate, and bone matrix gelatin.

21. The method of claim 13, wherein said ADAS cell is genetically modified.

22. The method of claim 13, wherein said ADAS cell is administered into one or more interbody spaces in the spine of said mammal.

23. The method of claim 13, wherein the spinal fusion is in a segment of the spine selected from the group consisting of cervical, thoracic, lumbar, lumbosacral and SI joint.

24. The method of claim 13, wherein said ADAS cell is administered into one or more interbody spaces by an approach selected from the group consisting of a posterior approach, a posterolateral approach, an anterior approach, an anterolateral approach, and a lateral approach.

25. The method of claim 13, wherein said mammal is a human.

* * * * *